(12) United States Patent
Endo et al.

(10) Patent No.: US 7,049,111 B1
(45) Date of Patent: May 23, 2006

(54) PROCESS FOR PRODUCING HMG-COA REDUCTASE INHIBITOR

(75) Inventors: Hirofumi Endo, Machida (JP); Yoshiyuki Yonetani, Machida (JP); Hiroshi Mizoguchi, Machida (JP); Shin-ichi Hashimoto, Hofu (JP); Akio Ozaki, Hofu (JP)

(73) Assignee: Kyowa Hakko Kogyo Co., Ltd., Tokyo (JP)

(*) Notice: Subject to any disclaimer, the term of this patent is extended or adjusted under 35 U.S.C. 154(b) by 0 days.

(21) Appl. No.: 09/869,334

(22) PCT Filed: Jan. 28, 2000

(86) PCT No.: PCT/JP00/00472

§ 371 (c)(1),
(2), (4) Date: Sep. 26, 2001

(87) PCT Pub. No.: WO00/44886

PCT Pub. Date: Mar. 8, 2000

(30) Foreign Application Priority Data

Jan. 29, 1999 (JP) .................................. 11/021707

(51) Int. Cl.
C12N 9/02 (2006.01)
C12N 15/00 (2006.01)
C12N 5/00 (2006.01)
C12N 1/20 (2006.01)
C12P 7/22 (2006.01)

(52) U.S. Cl. .................... 435/189; 435/320.1; 435/325; 435/252.3; 435/69.1; 435/156; 435/25; 435/252.31; 435/252.32; 435/252.33; 435/252.35; 435/125; 435/135; 435/136; 435/142; 435/146; 435/148; 536/23.2; 530/350

(58) Field of Classification Search ................ 435/189, 435/69.1, 25, 320.1, 252.3, 325, 156, 252.31, 435/252.32, 252.33, 252.35, 125, 135, 136, 435/142, 146, 148; 530/350; 536/23.2
See application file for complete search history.

(56) References Cited

U.S. PATENT DOCUMENTS

| | | | |
|---|---|---|---|
| 4,346,227 A | 8/1982 | Terahara et al. | |
| 4,410,629 A | 10/1983 | Terahara et al. | |
| 4,448,979 A | 5/1984 | Terahara et al. | |
| 4,537,859 A | 8/1985 | Terahara et al. | |
| 5,942,423 A | 8/1999 | Demain et al. | |
| 6,043,064 A | 3/2000 | Davis et al. | |
| 6,245,535 B1 | 6/2001 | Takano et al. | |

FOREIGN PATENT DOCUMENTS

| | | |
|---|---|---|
| EP | 0649907 | 4/1995 |
| EP | 1148122 | 10/2001 |
| JP | 57-50894 | 3/1982 |
| JP | 64-2585 | 1/1989 |
| JP | 2672551 | 1/1989 |
| JP | 7-184670 | 7/1995 |
| WO | 96/40863 | 12/1996 |
| WO | 99/07872 | 2/1999 |
| WO | 99/10499 | 3/1999 |
| WO | 99/60151 | 11/1999 |
| WO | 00/44886 | 8/2000 |

OTHER PUBLICATIONS

Kunst et al., GenBank accession No. CAB13078, Nov. 1997.*
Witkowski et al., Biochemistry 38:11643-11650, 1999.*
Seffernick et al., J. Bacteriol. 183(8):2405-2410, 2001.*
English Language Abstract of JP 57-50894.
English Language Abstract of JP 7-184670.
English Language Abstract of JP 64-2585.
The Journal of Antibiotics, 29, (1976), pp. 1346-1348.
www.pasteur.fr/Bio/SubtiList.html.
Kunst, F. et al., Nature, vol. 390, pp. 249-256 (1997).
Rivolta, C. et al., Microbiology, vol. 144, pp. 877-884 (1998).

(Continued)

Primary Examiner—Rebecca E. Prouty
Assistant Examiner—Delia M. Ramirez
(74) Attorney, Agent, or Firm—Greenblum & Bernstein, P.L.C.

(57) ABSTRACT

The present invention relates to a protein derived from a microorganism belonging to the genus *Bacillus*, which has an activity of hydroxylating a compound represented by the formula (I-a):

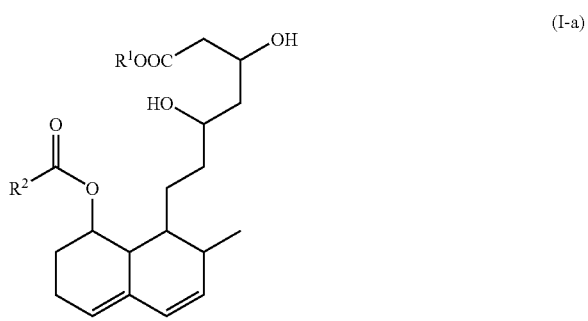

(I-a)

wherein $R^1$ represents a hydrogen atom, a substituted or unsubstituted alkyl, or an alkali metal, and $R^2$ represents a substituted or unsubstituted alkyl or a substituted or unsubstituted aryl,
or a ring-closed lactone form thereof;
a DNA encoding the protein; and a recombinant DNA comprising the DNA.

18 Claims, No Drawings

OTHER PUBLICATIONS

Alberts, A., Cardiology, vol. 77 (suppl 4), pp. 14-21 (1990).
U.S. Appl. No. 09/868,924, Hashimoto et al.
T. Okazaki et al., The Journal of Antibiotics, vol. 36, No. 9, Sep. 1983, pp. 1176-1183.
ATCC Website, downloaded from www.atcc.org/SearchCatalogs/Bacteria.cfm.
N. Serizawa, Biotechnology Annual Review, vol. 2, 1996, pp. 373-389.

* cited by examiner

PROCESS FOR PRODUCING HMG-CoA REDUCTASE INHIBITOR

TECHNICAL FIELD

The present invention relates to a DNA which is related to the production of a compound which inhibits hydroxymethylglutaryl CoA (HMG-CoA) reductase and has an action of reducing serum cholesterol, and a process for producing said compound using the DNA.

BACKGROUND ART

A compound represented by the formula (VI-a) (hereinafter referred to as compound (VI-a)):

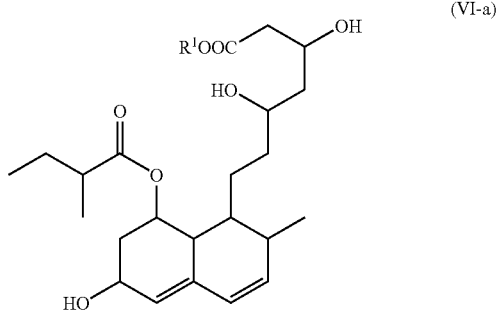

(VI-a)

wherein $R^1$ represents a hydrogen atom, a substituted or unsubstituted alkyl, or an alkali metal; or a lactone form of compound (VI-a) represented by the formula (VI-b) (hereinafter referred to as compound (VI-b)):

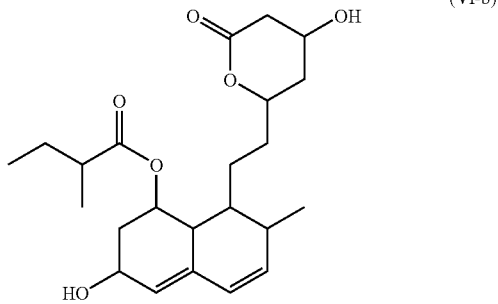

(VI-b)

is known to inhibit HMG-CoA reductase and exhibit an action of reducing serum cholesterol (*The Journal of Antibiotics*, 29, 1346 (1976)).

There have been several reports regarding methods for producing compound (VI-a) or compound (VI-b) from a compound represented by the formula (V-a) (hereinafter referred to as compound (V-a)):

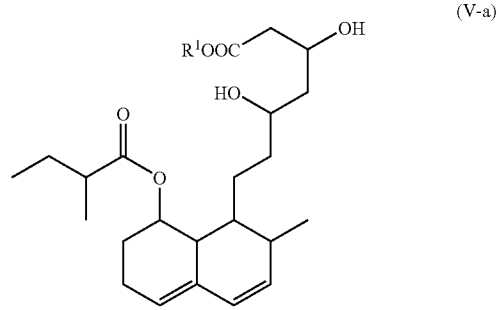

(V-a)

wherein $R^1$ has the same definition as the above; or from the lactone form of compound (V-a) represented by the formula (V-b) (hereinafter referred to as compound (V-b)):

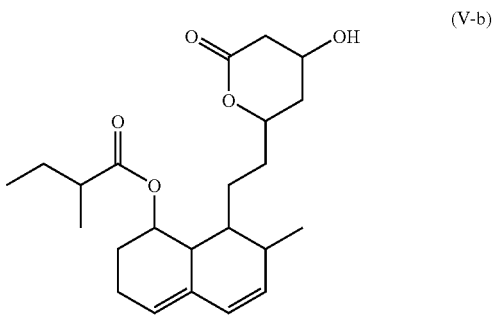

(V-b)

using a microorganism.

Specifically, Japanese Patent Application Laid-Open (kokai) No. 57-50894 describes a method which uses filamentous fungi; both Japanese Patent Application Laid-Open (kokai) No. 7-184670 and International Publication WO96/40863 describe a method which uses *Actinomycetes*; and Japanese Patent No. 2672551 describes a method which uses recombinant *Actinomycetes*. As is well known, however, since filamentous fungi and *Actinomycetes* grow with filamentaous form by elongating hyphae, the viscosity of the culture in a fermentor increases.

This often causes a shortage of oxygen in the culture, and since the culture becomes heterogeneous, reaction efficiency tends to be reduced. In order to resolve this oxygen shortage and maintain homogenousness of the culture, the agitation rate of the fermentor should be raised, but by raising the agitation rate, hyphae are sheared and, as a result, activity of the microorganisms tends to decrease (Basic Fermentation Engineering (Hakko Kogaku no Kiso) p. 169–190, P. E Stansbury, A. Whitaker, Japan Scientific Societies Press (1988)).

DISCLOSURE OF THE INVENTION

The object of the present invention is to provide a DNA encoding a novel hydroxylase, and an industrially advantageous method for producing a compound which inhibits HMG-CoA reductase and has an action of reducing the level of serum cholesterol.

The present inventors considered that, if the hydroxylation of compound (I-a) or compound (I-b) could be carried out with a microorganism forming no hyphae, inconvenience such as the decrease of reaction efficiency due to the heterogeneity of the culture caused by hyphae formation could be avoided, and that this would be industrially advantageous. Thus, as a result of intensive studies, the present inventors have accomplished the present invention.

Thus, the present invention relates to the following (1) to (39).

Hereinafter, in the formulas, $R^1$ represents a hydrogen atom, a substituted or unsubstituted alkyl, or an alkali metal, and $R^2$ represents a substituted or unsubstituted alkyl, or a substituted or unsubstituted aryl, unless otherwise specified.

(1) A protein which is derived from a microorganism belonging to the genus *Bacillus*, and has an activity of producing compound (II-a) or compound (II-b) from compound (I-a) or compound (I-b), wherein the compound (I-a) is a compound represented by the formula (I-a):

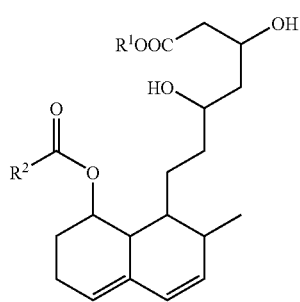
(I-a)

the compound (I-b) is a lactone form of compound (I-a) and is represented by the formula (I-b):

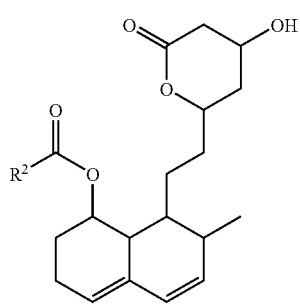
(I-b)

the compound (II-a) is a compound represented by the formula (II-a):

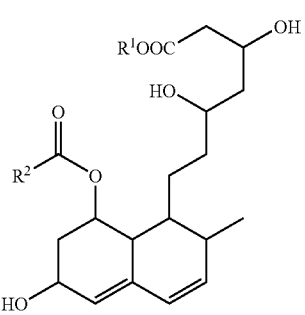
(II-a)

the compound (I-b) is a lactone form of compound (II-a) and is represented by the formula (II-b):

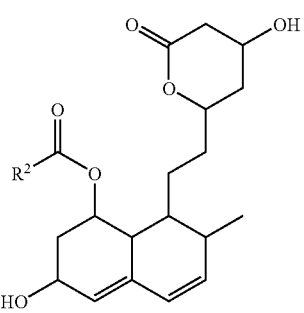
(II-b)

(2) A protein which is derived from a microorganism belonging to the genus *Bacillus*, and has an activity of producing compound (IV-a) or compound (IV-b) from compound (III-a) or compound (II-b), wherein the compound (III-a) is a compound represented by the formula (III-a):

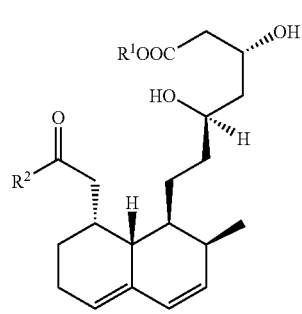
(III-a)

the compound (III-b) is a lactone form of compound (III-a) and is represented by the formula (III-b):

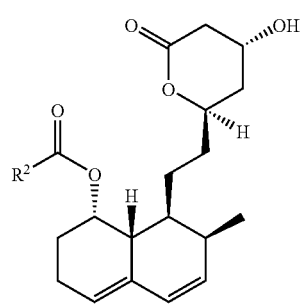
(III-b)

the compound (IV-a) is a compound represented by the formula (IV-a):

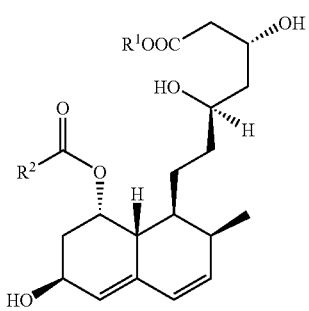
(IV-a)

the compound (IV-b) is a lactone form of compound (IV-a) and is represented by the formula (IV-b):

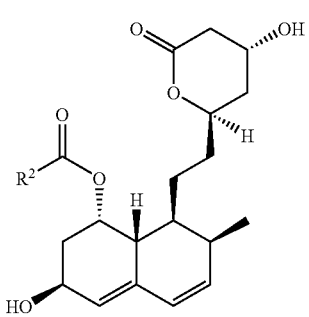
(IV-b)

(3) A protein which is derived from a microorganism belonging to the genus *Bacillus*, and has an activity of producing compound (VI-a) or compound (VI-b) from compound (V-a) or compound (V-b), wherein the compound (V-a) is a compound represented by the formula (V-a):

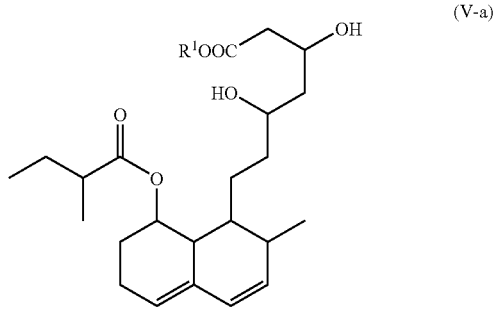

(V-a)

the compound (V-b) is a lactone form of compound (V-a) and is represented by the formula (V-b):

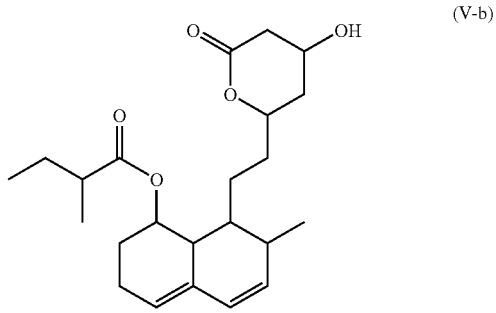

(V-b)

the compound (VI-a) is a compound represented by the formula (VI-a):

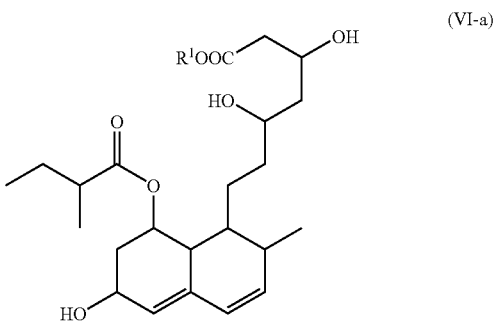

(VI-a)

; and the compound (VI-b) is a lactone form of compound (VI-a) and is represented by the formula (VI-b):

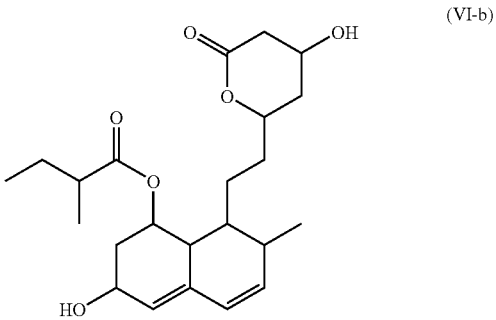

(VI-b)

(4) A protein which is derived from a microorganism belonging to the genus *Bacillus*, and has an activity of producing compound (VIII-a) or compound (VIII-b) from compound (VII-a) or compound (VII-b), wherein the compound (VII-a) is a compound represented by the formula (VII-a):

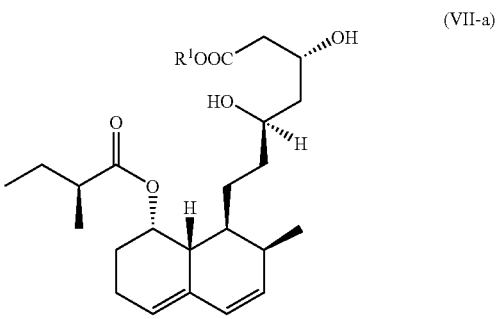

(VII-a)

the compound (VII-b) is a lactone form of compound (VII-a) and is represented by the formula (VII-b):

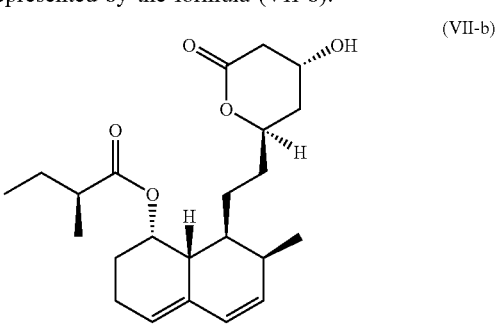

(VII-b)

the compound (VIII-a) is a compound represented by the formula (VIII-a):

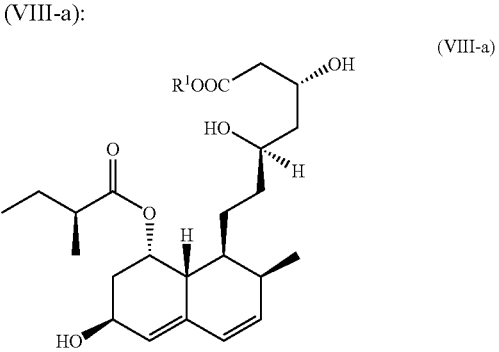

(VIII-a)

; and the compound (VIII-b) is a lactone form of compound (VIII-a) and is represented by the formula (VIII-b):

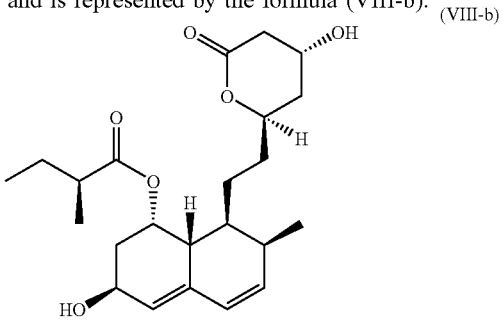

(VIII-b)

(5) The protein according to any one of (1) to (4) above, wherein the microorganism belonging to the genus *Bacillus* is a microorganism selected from *B. subtilis, B. megaterium, B. laterosporus, B. sphaericus, B. pumilus, B. stearothermophilus, B. cereus, B. badius, B. brevis, B. alvei, B. circulars* and *B. macerans.*

(6) The protein according to any one of (1) to (5) above, wherein the microorganism belonging to the genus *Bacillus* is a microorganism selected from *B. subtilis* ATCC6051, *B. megaterium* ATCC10778 *B. megaterium* ATCC11562, *B. megaterium* ATCC13402, *B. megaterium* ATCC15177, *B. megaterium* ATCC15450, *B. megaterium* ATCC19213, *B. megaterium* IAM1032, *B. laterosporus* ATCC4517, *B. pumilus* FERM BP-2064, *B. badius* ATCC14574, *B. brevis* NRRL B-8029, *B. alvei* ATCC6344, *B. circulars* NTCT-2610, and *B. macerans* NCIMB-9368.

(7) The protein according to any one of (1) to (5) above, wherein the microorganism belonging to the genus *Bacillus* is a microorganism selected from *Bacillus* sp. FERM BP-6029 or *Bacillus* sp. FERM BP-6030.

(8) A protein having the amino acid sequence shown by SEQ ID NO: 1.

(9) A protein which has an amino acid sequence comprising deletion, substitution or addition of one or more amino acids in the amino acid sequence shown by SEQ ID NO: 1, and has an activity of producing compound (II-a) or compound (II-b) from compound (I-a) or compound (I-b).

(10) The protein according to (9) above, wherein the protein has the amino acid sequence shown by SEQ ID NO: 42 or 45.

(11) The protein according to (9) above, wherein the compound (I-a) is compound (III-a), the compound (I-b) is compound (III-b), the compound (II-a) is compound (IV-a), and the compound (II-b) is compound (IV-b).

(12) The protein according to (9) above, wherein the compound (I-a) is compound (V-a), the compound (I-b) is compound (V-b), the compound (II-a) is compound (VI-a), and the compound (II-b) is compound (VI-b).

(13) The protein according to (9) above, wherein the compound (I-a) is compound (VII-a), the compound (I-b) is compound (VII-b), the compound (II-a) is compound (VIII-a), and the compound (II-b) is compound (VIII-b).

(14) An isolated DNA having the nucleotide sequence shown by SEQ ID NO: 2.

(15) An isolated DNA which hybridizes with the DNA according to (14) above under stringent conditions, and encodes a protein having an activity of producing compound (II-a) or compound (I-b) from compound (I-a) or compound (I-b).

(16) The DNA according to (15) above, wherein the DNA has a nucleotide sequence selected from the group consisting of the nucleotide sequences shown by SEQ ID NOS: 41, 43 and 44.

(17) An isolated DNA encoding the protein according to any one of (1) to (12) above.

(18) The DNA according to (15) above, wherein the compound (I-a) is compound (III-a), the compound (I-b) is compound (III-b), the compound (II-a) is compound (IV-a), and the compound (II-b) is compound (IV-b).

(19) The DNA according to (15) above, wherein the compound (I-a) is compound (V-a), the compound (I-b) is compound (V-b), the compound (II-a) is compound (VI-a), and the compound (II-b) is compound (VI-b).

(20) The DNA according to (15) above, wherein the compound (I-a) is compound (VII-a), the compound (I-b) is compound (VII-b), the compound (II-a) is compound (VIII-a), and the compound (II-b) is compound (VIII-b).

(21) A recombinant DNA vector comprising the DNA according to any one of (14) to (20) above.

(22) A transformant obtained by introducing the recombinant DNA vector according to (21) above into a host cell.

(23) The transformant according to (22) above, wherein the transformant belongs to a microorganism selected from the genera *Escherichia, Bacillus, Corynebacterium,* and *Streptomyces.*

(24) The transformant according to (22) or (23) above, wherein the transformant belongs to microorganism selected from *Escherichia coli, Bacillus subtilis, Bacillus megaterium, Corynebacterium glutamicum, Corynebacterium ammoniagenes, Corynebacterium callunae* and *Streptomyces lividans.*

(25) A process for producing compound (II-a) or compound (II-b), wherein the transformant according to any one of (22) to (24) above, a culture of the transformant, or a treated product of the culture is used as an enzyme source, and the process comprises:

allowing compound (I-a) or compound (I-b) to exist in an aqueous medium;

allowing compound (II-a) or compound (II-b) to be produced and accumulated in said aqueous medium; and collecting compound (II-a) or compound (II-b) from said aqueous medium.

(26) A process for producing compound (IV-a) or compound (IV-b), wherein the transformant according to any one of (22) to (24) above, a culture of the transformant, or a treated product of the culture is used as an enzyme source, and the process comprises:

allowing compound (III-a) or compound (III-b) to exist in an aqueous medium;

allowing compound (IV-a) or compound (IV-b) to be produced and accumulated in said aqueous medium; and collecting compound (IV-a) or compound (IV-b) from said aqueous medium.

(27) A process for producing compound (VI-a) or compound (VI-b), wherein the transformant according to any one of (22) to (24) above, a culture of the transformant, or a treated product of the culture is used as an enzyme source, and the process comprises:

allowing compound (V-a) or compound (V-b) to exist in an aqueous medium;

allowing compound (VI-a) or compound (VI-b) to be produced and accumulated in said aqueous medium; and collecting compound (VI-a) or compound (VI-b) from said aqueous medium.

(28) A process for producing compound (VIII-a) or compound (VIII-b), wherein the transformant according to any one of (22) to (24) above, a culture of the transformant, or a treated product of the culture is used as an enzyme source, and the process comprises:

allowing compound (VII-a) or compound (VII-b) to exist in an aqueous medium;

allowing compound (VIII-a) or compound (VIII-b) to be produced and accumulated in said aqueous medium; and collecting compound (VIII-a) or compound (VIII-b) from said aqueous medium.

(29) The process according to (25) above, wherein the compound (II-b) is the compound (II-b) obtained by forming a lacton from compound (II-a).

(30) The process according to (25) above, wherein the compound (II-a) is the compound (II-a) obtained by opening the lactone ring of compound (II-b).

(31) The process according to (26) above, wherein the compound (IV-b) is the compound (IV-b) obtained by forming a lacton from compound (IV-a).

(32) The process according to (26) above, wherein the compound (IV-a) is the compound (IV-a) obtained by opening the lactone ring of compound (IV-b).

(33) The process according to (27) above, wherein the compound (VI-b) is the compound (VI-b) obtained by forming a lacton from compound (VI-a).

(34) The process according to (27) above, wherein the compound (VI-a) is the compound (VI-a) obtained by opening the lactone ring of compound (VI-b).

(35) The process according to (28) above, wherein the compound (VIII-b) is the compound (VIII-b) obtained by forming a lacton from compound (VIII-a).

(36) The process according to (28) above, wherein the compound (VIII-a) is the compound (VIII-a) obtained by opening the lactone ring of compound (VIII-b).

(37) The process according to any one of (25) to (28) above, wherein the treated product of the culture of the transformant is a treated product selected from cultured cells; treated products such as dried cells, freeze-dried cells, cells treated with a surfactant, cells treated with an enzyme, cells treated by ultrasonication, cells treated by mechanical milling, cells treated by solvent; a protein fraction of a cell; and an immobilized products of cells or treated cells.

(38) A process for producing a protein, which comprises culturing the transformant according to any one of (22) to (24) above in a medium; producing and accumulating the protein according to any one of (1) to (12) above in the culture; and collecting said protein from said culture.

(39) An oligonucleotide corresponding to a sequence consisting of 5 to 60 continuous nucleotides in a nucleotide sequence selected from the group consisting of the nucleotide sequences shown by SEQ ID NOS: 2, 41, 43 and 44; or an oligonucleotide corresponding to a complementary sequence to said oligonucleotide.

The present invention will be described in detail below.

1. Obtaining of yjiB Gene

The DNA of the present invention can be obtained by PCR method [Science, 230, 1350 (1985)] using the genome nucleotide sequence information of a chromosome of *Bacillus subtilis* which has already been determined [http://www.pasteur.fr/Bio/SubtiList.html] and the information on *Bacillus subtilis* yjiB gene deduced from said genome nucleotide sequence.

Specifically, the DNA of the present invention can be obtained by the following method.

*Bacillus subtilis* (e.g., *B. subtilis* ATCC15563) is cultured by a usual manner in a medium suitable for *Bacillus subtilis*, e.g. LB liquid medium [containing Bacto Trypton (produced by Difco) 10 g, yeast extract (produced by Difco) 5 g, and NaCl 5 g in 1 L of water; and adjusted to pH 7.2]. After culturing, the cells are collected from the culture by centrifugation.

A chromosomal DNA is isolated from the collected cells by a known method (e.g., Molecular Cloning $2^{nd}$ ed).

Using the nucleotide sequence information shown by SEQ ID NO:2, sense and antisense primers containing nucleotide sequences corresponding to the DNA region encoding a protein of the present invention are synthesized with a DNA synthesizer.

After amplification by PCR, in order to enable introduction of said amplified DNA fragments into a plasmid, it is preferred that an appropriate restriction site such as BamHI, EcoRI or the like is added at 5' end of the sense and antisense primers.

Examples of combinations of said sense and antisense primers include combination of DNAs having nucleotide sequences shown by SEQ ID NOS:13 and 14.

Using chromosomal DNA as a template, PCR is performed with these primers, TaKaRa LA-PCR™ Kit Ver. 2 (TaKaRa), Expand™ High-Fidelity PCR System (Boehringer Mannheim) or the like by a DNA Thermal Cycler (Perkin-Elmer Japan).

When PCR is performed, for example, the following method can be carried out. In the case where the above primer is a DNA fragment of 2 kb or less, each cycle consists of reaction steps of 30 seconds at 94° C., 30 seconds to 1 minute at 55° C., and 2 minutes at 72° C. In the case where the above primer is a DNA fragment of more than 2 kb, each cycle consists of reaction steps of 20 seconds at 98° C. and 3 minutes at 68° C. In any case, PCR is performed under conditions where the 30 cycles are repeated, and then reaction is carried out for 7 minutes at 72° C.

The amplified DNA fragments are cut at the same restriction site as the site which is formed using the above primers, and then the DNA fragments are fractioned and recovered by a method such as agarose gel electrophoresis, sucrose density gradient ultracentrifugation and the like.

Using the recovered DNA fragments, a cloning vector is produced by a usual method such as methods described in Molecular Cloning $2^{nd}$ ed., Current Protocols in Molecular Biology, Supplement 1–38, John Wiley & Sons (1987–1997) (abbreviated as Current Protocols in Molecular Biology, Supplement hereinafter), DNA Cloning 1: Core Techniques, A Practical Approach, Second Edition, Oxford University Press (1995), or by using a commercially available kit such as SuperScript Plasmid System for cDNA Synthesis and Plasmid Cloning (produced by Life Technologies), ZAP-cDNA Synthesis Kit (produced by Stratagene), etc., then the thus-produced cloning vector is used to transform *Escherichia coli*, e.g. *E. coli* DH5 α strain (available from TOYOBO).

Examples of a cloning vector for the transformation of *E. coli* include a phage vector and plasmid vector insorfar as it is capable of self-replicating in *E. coli* K12 strain. An expression vector for *E. coli* can also be used as a cloning vector. Specifically, examples thereof include ZAP Express [produced by Stratagene, Strategies, 5, 58 (1992)], pBluescript II SK(+) [Nucleic Acids Research, 17, 9494 (1989)], Lambda ZAP II (produced by Stratagene), λgt10, λgt11 [DNA Cloning, A Practical Approach, 1, 49 (1985)], λTriplEx (produced by Clonetech), λExCell (produced by Pharmacia), pT7T318U (produced by Pharmacia), pcD2 [H. Okayama and P. Berg; Mol. Cell. Biol., 3, 280 (1983)], pMW218 (produced by Wako Pure Chemical Industries), pUC118, pSTV28 (produced by Takara), pEG400 [J. Bac., 172, 2392 (1990)], pHMV1520 (produced by MoBiTec), pQE-30 (produced by QIAGEN), etc.

A plasmid containing a desired DNA can be obtained from the obtained transformed strain by usual methods described in e.g. Molecular Cloning $2^{nd}$ edition, Current Protocols in Molecular Biology Supplement, DNA Cloning 1: Core Techniques, A Practical Approach, Second Edition, and Oxford University Press (1995), etc.

Using the aforementioned method, a plasmid containing a DNA encoding a protein which catalyzes reaction of producing compound (II-a) or compound (I-b) from compound (I-a) or compound (I-b), can be obtained.

Examples of the plasmids include the below-mentioned pSyjiB.

Apart from the aforementioned method, a plasmid containing a DNA encoding a protein which catalyzes a reaction of producing compound (II-a) or compound (II-b) from compound (I-a) or compound (I-b) can be obtained also by a method wherein a chromosomal library of *Bacillus subtilis* is prepared with a suitable vector using *E. coli* as a host, and the activity of producing compound (II-a) or compound (II-b) from compound (I-a) or compound (I-b) is measured on each strain of this library.

The nucleotide sequence of the above-obtained gene can be used to obtain homologues of the DNA from other prokaryotes or plants in the same manner as mentioned above.

The DNA and DNA fragment of the present invention obtained in the above method can be used to prepare oligonucleotides such as antisense oligonucleotides, sense oligonucleotides etc. having a partial sequence of the DNA of the present invention or such oligonucleotides containing RNAs. Alternatively, based on the sequence information of the above-obtained DNA, these oligonucleotides can be synthesized with the above DNA synthesizer.

Examples of the oligonucleotides include a DNA having the same sequence as a contiguous 5 to 60 nucleotides in the nucleotide sequence of the above DNA, or a DNA having a complementary sequence to said DNA. RNAs having complementary sequences to these DNAs are also oligonucleotides of the present invention.

Examples of said oligonucleotides include a DNA having the same sequence as a contiguous 5 to 60 nucleotides sequence in the nucleotide sequences shown by SEQ ID NOS:2, 41, 43 or 44, or a DNA having a complementary sequence to said DNA. If these are used as sense and antisense primers, the aforementioned oligonucleotides without extreme difference in melting temperatures (Tm) and numbers of bases are preferably used. Specifically, examples thereof include oligonucleotides having a nucleotide sequence shown by SEQ ID NOS: 3 to 39.

Furthermore, derivatives of these oligonucleotides (referred to as oligonucleotide derivative hereinafter) can also be used as the DNA of the present invention.

Oligonucleotide derivatives include a oligonucleotide derivative whose phosphate diester linkage is replaced by a phosphorothioate linkage, an oligonucleotide derivative whose phosphate diester linkage is replaced by a N3'-P5' phosphoamidate linkage, an oligonucleotide derivative whose ribose and phosphate diester linkage is replaced by a peptide-nucleic acid linkage, an oligonucleotide derivative whose uracil is replaced by C-5 propinyl uracil, an oligonucleotide derivative whose uracil is replaced by C-5 thiazol uracil, an oligonucleotide derivative whose cytosine is replaced by C-5 propinyl cytosine, an oligonucleotide derivative whose cytosine is replaced by phenoxazine-modified cytosine, an oligonucleotide derivative whose ribose is replaced by 2'-O-propyl ribose, or an oligonucleotide derivative whose ribose is replaced by 2'-methoxy-ethoxyribose, etc. [Saibo Kogaku, 16, 1463 (1997).]

II. Method for Producing a Protein which Catalyzes a Reaction of Producing Compound (II-a) or Compound (II-b) from Compound (I-a) or Compound (I-b)

In order to express the above-obtained DNA in a host cell, the desired DNA fragment is cut into a fragment of suitable length containing said gene using restriction enzymes or DNase enzymes, followed by inserting the fragment into a site downstream of a promoter in an expression vector, and then the expression vector is introduced into host cells suitable for use of the expression vector.

The host cells may be any of bacteria, yeasts, animal cells, insect cells or the like insofar as they can express the objective gene.

As an expression vector, a vector capable of being autonomously replicated in a host cell or capable of being integrated into a chromosome, and containing a promoter at a site suitable for transcription of the above objective gene, is used.

When prokaryotes such as bacteria are used as the host cell, the expression vector for expressing the above DNA is preferably a vector autonomously replicable in said cell and is a recombinant vector composed of a promoter, a ribosome-binding sequence, the above DNA and a transcription termination sequence. A gene for regulating the promoter may be contained.

The expression vectors include pBTrp2, pBTac1, pBTac2 (all of which are commercially available from Boehringer Mannheim), pKK233-2 (produced by Pharmacia), pSE280 (produced by Invitrogen), pGEMEX-1 (produced by Promega), pQE-8 (produced by QIAGEN), pQE-30 (produced by QIAGEN), pKYP10 (Japanese Patent Application Laid-Open No. 58-110600), pKYP200 [Agricultural Biological Chemistry, 48, 669 (1984)], pLSA1 [Agric. Biol. Chem., 53, 277 (1989)], pGEL1 [Proc. Natl. Acad. Sci., USA, 82, 4306 (1985)], pBluescriptII SK(+), pBluescriptII SK(−) (produced by Stratagene), pTrS30 (FERM BP-5407), pTrS32 (FERM BP-5408), pGEX (produced by Pharmacia), pET-3 (produced by Novagen), pTerm2 (U.S. Pat. No. 4,686,191, U.S. Pat. No. 4,939,094, U.S. Pat. No. 5,160,735), pSupex, pUB110, pTP5, pC194, pUC18 [gene, 33, 103 (1985)], pUC19 [Gene, 33, 103 (1985)], pSTV28 (produced by Takara), pSTV29 (produced by Takara), pUC118 (produced by Takara), pPA1 (Japanese Patent Application Laid-Open No. 63-233798), pEG400 [J. Bacteriol., 172, 2392 (1990)], pQE-30 (produced by QIAGEN), PHY300 (produced by Takara), pHW1520 (produced by MoBiTec), etc.

The promoter may be any one insofar as it can be expressed in a host cell. Examples are promoters derived from *E. coli*, phage etc., such as trp promoter (Ptrp), lac promoter (Plac), PL promoter, PR promoter and PSE promoter, and SP01 promoter, SP02 promoter, penP promoter and the like. Artificially designed and modified promoters such as a Ptrp×2 promoter having two Ptrp promoters in tandem, tac promoter, letI promoter, and lacT7 promoter can also be used. Furthermore, xylA promoter for expression in Bacillus bacteria or P54-6 promoter for expression in Corynebacterium bacteria can also be used.

Any ribosome binding sequences may be used insofar as they can work in a host cell, and a plasmid in which the distance between a Shine-Dalgarno sequence and an initiation codon is adjusted to an appropriate distance (for example, 6 to 18 bases) may be preferably used.

For efficient transcription and translation, a protein which catalyzes the reaction of producing compound (II-a) or compound (II-b) from compound (I-a) or compound (I-b) wherein the N-terminus or a part thereof is deleted may be fused to the N-terminus part of a protein encoded by the expression vector, and the thus-obtained fused protein may be expressed. Such examples include the below-mentioned pWyjiB.

Although a transcription termination sequence is not necessarily required for expression of the desired DNA, it is preferred to locate the transcription termination sequence just downstream from the structural gene.

Examples of prokaryotes include microorganisms belonging to the genus *Escherichia, Corynebacterium, Brevibacterium, Bacillus, Microbacterium, Serratia, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Streptomyces, Synechococcus,* and *Zymomonas,* preferably *Escherichia, Corynebacterium, Brevibacterium, Bacillus, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Streptomyces, Synechococcus,* and *Zymomonas.*

Specific examples of the microorganisms include *Escherichia coli* XL1-Blue, *Escherichia coli* XL2-Blue, *Escherichia coli* DH1, *Escherichia coli* DH5 α, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Escherichia coli* MP347, *Escherichia coli* NM522, *Bacillus subtilis* ATCC33712, *Bacillus megaterium Bacillus* sp. FERM BP-6030, *Bacillus amyloliquefacines, Brevibacterium ammmoniagenes, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Corynebacterium callunae* ATCC15991, *Microbacterium ammoniaphilum* ATCC15354, *Serratia ficaria, Serratia fonticola, Serratia liquefaciens, Serratia marcescens, Pseudomonas* sp. D-0110, *Agrobacterium radiobacter, Agrobacterium rhizogenes, Agrobacterium rubi, Anabaena cylindrical, Anabaena doliolum, Anabaena flos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfurous, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium* sp. ATCC29409, *Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus,* and *Zymomonas mobilis.*

The method for introducing the recombinant vector may be any method for introducing DNA into the host cells described above. For examples, mention can be made of a method using calcium ions [Proc. Natl. Acad. Sci. USA, 69, 2110 (1972)], a protoplast method (Japanese Patent Application Laid-Open No. 63-248394), an electroporation method, a method described in Gene, 17, 107 (1982) and Molecular & General Genetics, 168, 111 (1979), and the like.

If yeasts are used as the host cell, expression vectors such as YEp13 (ATCC37115), YEp24 (ATCC37051), YCp50 (ATCC37419), pHS19, and pHS15 can be exemplified.

Any promoter can be used insofar as they can be expressed in yeasts. For example, mention can be made of promoters such as PHO5 promoter, PGK promoter, GAP promoter, ADH promoter, gal 1 promoter, gal 10 promoter, heat shock protein promoter, MFα1 promoter, and CUP 1 promoter.

Examples of host cells include *Saccharomyces cerevisiae, Schizosaccharomyces pombe, Kluyveromyces lactis, Trichosporon pullulans,* and *Schwanniomyces alluvius.*

The method for introducing a recombinant vector may be any method for introducing DNA into yeast, and examples include an electroporation method [Methods Enzymol., 194, 182 (1990)], a speroplast method [Proc. Natl. Acad. Sci. USA, 75, 1929 (1978)], a lithium acetate method [J. Bacteriol., 153, 163 (1983)] and a method describe in Proc. Natl. Acad. Sci. USA, 75, 1929 (1978).

If animal cells are used as the host cells, expression vectors such as pcDNAI, pcDM8 (commercially available from Funakoshi), pAGE107 (Japanese Patent Application Laid-Open No. 3-22979; Cytotechnology, 3, 133 (1990)), pAS3-3 (Japanese Patent Application Laid-Open No. 2-227075), pCDM8 [Nature, 329, 840 (1987)], pcDNAI/Amp (Invitrogen), pREP4 (Invitrogen), pAGE103 [J. Biochem., 101, 1307 (1987)], and pAGE210 can be used.

The promoter to be used may be any promoter which can be expressed in animal cells. Examples are a promoter for IE (immediate early) gene of cytomegalovirus (human CMV), SV40 early promoter, retrovirus promoter, metallothionein promoter, heat shock promoter, Sr α promoter and the like. Furthermore, an enhancer of the IE gene of human CMV may be used together with a promoter.

Examples of animal cells include Namalwa cell, HBT5637 (Japanese Patent Application Laid-Open No. 63-299), COS1 cell, COS7 cell, CHO cell and the like.

The method for introducing a recombinant vector into animal cells may be any method for introducing DNA into animal cells. Examples of such methods include an electroporation method [Cytotechnology, 3, 133 (1990)], a calcium phosphate method (Japanese Patent Application Laid-Open No. 2-227075), a lipofection method [Proc. Natl. Acad. Sci., USA, 84, 7413 (1987)], a method described in Virology, 52, 456 (1973), and the like. Obtaining and culturing of the transformant can be conducted according to methods described in Japanese Patent Application Laid-Open No. 2-227075 or Japanese Patent Application Laid-Open No. 2-257891.

If insect cells are used as the host cells, the protein can be expressed by methods described in Baculovirus Expression Vectors, A Laboratory Manual, Current Protocols in Molecular Biology Supplement 1–38 (1987–1997); Bio/Technology, 6, 47 (1988) and the like.

That is, a recombinant gene transfer vector and a baculovirus are co-transfected into insect cells to obtain a recombinant virus in the culture supernatant of the insect cells, and then the insect cells are infected with the recombinant virus whereby the protein can be expressed.

Examples of the gene transfer vectors used in this method include pVL1392, pVL1393 and pBlueBacIII (all manufactured by Invitrogen).

As the baculovirus, it is possible to employ, e.g. *Autographa californica* nuclear polyhedrosis virus, that is, a virus infecting insects of the family Barathra.

As the insect cells, it is possible to use Sf9, Sf21 [Baculovirus Expression Vectors, A Laboratory Manual, W.H. Freeman and Company, New York (1992)] which are oocytes of *Spodoptera frugiperda* and High 5 (Invitrogen) which is oocyte of *Trichoplusia ni*, and the like.

As a method for co-transfering the aforesaid recombinant gene transfer vector and the aforesaid baculovirus into insect cells for preparing the recombinant virus, for example, a calcium phosphate method (Japanese Patent Application Laid-Open No. 2-227075), a lipofection method [Proc. Natl. Acad. Sci. USA, 84, 7413 (1987)] and the like may be used.

As a method for expressing gene, in addition to direct expression, secretory production, expression of a fusion protein and the like can be carried out according to the method described in Molecular Cloning 2$^{nd}$ edition.

When a protein has been expressed by yeasts, animal cells or insect cells, the protein to which a sugar or sugar chain is added can be obtained.

The thus-obtained transformant is cultured in a medium to produce and accumulate proteins which catalyze the reaction of producing compound (II-a) or compound (II-b) from compound (I-a) or compound (I-b) in the culture, and the proteins are recovered from the culture, thereby producing the protein which catalyzes production of compound (II-a) or compound (II-b) from compound (I-a) or compound (I-b).

As a method for culturing in a medium the transformant for the production of the protein of the present invention which catalyzes the reaction of producing compound (II-a) or compound (II-b) from compound (I-a) or compound (I-b), conventional methods used for culturing a transformant in a host cell can be used.

If the transformant of the present invention is a prokaryote such as *E. coli* or an eukaryote such as yeast, the medium for culturing these organisms may be either a natural or synthetic medium insofar as it contains a carbon source, a nitrogen source, inorganic salts and the like which can be assimilated by said organisms, and it allows efficient culturing of the transformant.

As a carbon source, any carbon source can be used as long as it can be assimilated by the microorganisms, including carbohydrates such as glucose, fructose, sucrose, or molasses containing those sources, starch or starch hydrolysates; organic acids such as acetic acid, propionic acid; and alcohols such as ethanol, propanol.

As a nitrogen source, the following can be used: ammonia; ammonium salts of various inorganic acids and organic acids, such as ammonium chloride, ammonium sulfate, ammonium acetate, and ammonium phophate; other nitrogen-containing compounds; and peptone, meat extracts, yeast extracts, corn steep liquor, caselin hydrolysates, soy bean meal, soy bean meal hydrolysates, various fermented cells and hydrolysates thereof, and the like.

Examples of the inorganic substances include potassium dihydrogenphosphate, potassium hydrogenphosphate, magnesium phosphate, magnesium sulfate, sodium chloride, ferrous sulfate, manganese sulfate, copper sulfate and calcium carbonate.

The culturing is carried out under aerobic conditions by shake culturing or aeration-agitation culturing or the like. The culturing temperature is preferably 15 to 50° C., and the culturing period is usually 16 hours to 7 days. While culturing, pH is maintained at 3.0 to 9.0. The pH control is conducted using an inorganic or organic acid, alkaline solution, urea, calcium carbonate, ammonia and the like.

If necessary, antibiotics such as ampicillin and tetracycline may be added to the medium while culturing.

When a microorganism transformed with an expression vector using an inductive promoter as a promoter is cultured, an inducer may be optionally added to the medium. For example, isopropyl-β-D-thiogalactopyranoside (IPTG), indole acrylic acid (IAA) or xylose may be added to the medium respectively, when a microorganism transformed with expression vectors containing lac promoter, trp promoter, or xylA promoter is used.

The medium for culturing the transformant obtained by using animal cells as host cells may be a generally-used medium such as RPMI1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] or any one of these media further supplemented with fetal calf serum.

Culturing is usually carried out for 1 to 7 days at pH 6 to 8 at 30 to 40° C. in the presence of 5% $CO_2$.

If necessary, antibiotics such as kanamycin and penicillin may be added to the medium while culturing.

The medium for culturing the transformant obtained by using insect cells as host cells may be a generally-used medium such as TNM-FH medium (produced by Pharmingen), Sf-900 II SFM medium (produced by Gibco BRL), ExCell 400 and ExCell 405 [both are products of JRH Biosciences], Grace's Insect Medium [Grace, T. C. C., Nature, 195, 788 (1962)] or the like.

Culturing is usually carried out at pH 6 to 7 at a temperature of 25 to 30° C. for a period of 1 to 5 days.

If necessary, antibiotics such as gentamycin may be added to the medium while culturing.

For isolating and purifying the protein which catalyzes a reaction of producing compound (II-a) or compound (II-b) from compound (I-a) or compound (I-b) from the culture of the transformant of the present invention, any conventional methods for the isolation and purification of enzymes can be performed.

For example, in the case where the protein of the present invention is expressed in a soluble form in cells, after culturing, the cells are recovered by centrifugation and suspended in an aqueous buffer, followed by disruption with ultrasonic disrupter, French Press, Manton-Gaulin homogenizer, Dynomill or the like, thereby obtaining a cell-free extract. From the supernatant obtained by centrifuging the cell-free extract, a purified preparation can be obtained by using conventional methods for isolation and purification of enzymes alone or in combination, such as solvent extraction, salting-out or desalting with sulfate ammonium etc., precipitation with an organic solvent, anion-exchange chromatography on resin such as diethylaminoethyl (DEAE)-Sepharose, DIAION HPA-75 (produced by Mitsubishi Chemical Industries Ltd.) or the like, cation-exchange chromatography on resin such as S-Sepharose FF (Pharmacia) or the like, hydrophobic chromatography on resin such as butyl Sepharose, phenyl Sepharose or the like, gel filtration using molecular sieve, affinity chromatography, chromatofocusing, and electrophoresis such as isoelectric electrophoresis.

In the case where the protein is expressed in a form of an inclusion body in cells, the cells are similarly recovered, disrupted and centrifuged, thereby obtaining a precipitated fraction, and the protein is recovered from the fraction in a usual manner. The recovered inclusion body is solubilized with a protein denaturating agent. The solubilized solution is then diluted with or dialyzed against a solution not containing the protein denaturating agent or a solution containing the protein denaturating agent at a concentration low enough not to denature the protein, whereby the protein is renatured to have normal tertiary structure, and its purified preparation can be obtained by the same isolation and purification method as described above.

When the protein of the present invention or a saccharide modified derivatives thereof are extracellularly secreted, the protein or the derivatives to which saccharide chain is added, can be recovered from the supernatant of the culture. That is, the culture is subjected to an above-mentioned process such as centrifugation and the like, thereby obtaining soluble fractions, then a purified preparation can be obtained from said soluble fractions in the same manner as in the above.

Examples of the thus-obtained proteins include proteins having amino acid sequences shown by SEQ ID NOS: 1, 42 or 45. Furthermore, the protein expressed in the above manner can also be produced by chemically synthesis methods such as Fmoc method (fluorenyl methyloxycarbonyl method) and tBoc method (t-butyloxycarbonyl method). Alternatively, the protein can be obtained by synthesis using a peptide synthesizer manufactured by Sowa Trading (Advanced chemTech, USA), Perkin-Elmer Japan (Perkin Elmer, USA), Pharmacia Biotech (Pharmacia Biotech, Sweden), ALOKA (Protein Technology Instrument, USA), KURABO (Synthecell-Vega, USA), Japan PerSeptive Ltd. (PerSeptive, USA), Shimazu, etc.

III. Production of Compound (II-a) or Compound (I-b)

Using cells obtained by culturing the transformant obtained in above II according to the method described in above II, a culture of said cells, a treated product of said culture, or an enzyme extracted from said cells as enzyme sources, compound (II-a) or compound (II-b) can be produced by allowing compound (I-a) or compound (I-b) to exist in an aqueous medium, allowing compound (II-a) or compound (I-b) to be produced and accumulated in the above aqueous medium, and collecting compound (II-a) or compound (I-b) from the above aqueous medium.

Examples of treated products of the culture of the cells include the treated products of the cells such as dried cells, lyophiled cells, cells treated with surfactants, cells treated with enzymes, cells treated with ultrasonication, cells treated with mechanical milling, cells treated with solvents; or protein fractions of the cells; or immobilized products of said cell and said treated products of said cells.

As a method for converting compound (I-a) or compound (I-b) into compound (II-a) or compound (II-b), both of the following methods (a) and (b) can be used: (a) a method wherein the compound (I-a) or compound (I-b) is previously added to the medium for culturing cells; and (b) a method wherein compound (I-a) or compound (I-b) is added to the medium while culturing. Alternatively, a method wherein the enzyme source obtained from the cell culture is reacted with compound (I-a) or compound (I-b) in the aqueous medium can be also used.

In a case where compound (I-a) or compound (I-b) is added to a medium in which a microorganism is to be cultured, 0.1 to 10 mg, preferably 0.2 to 1 mg of compound (I-a) or compound (I-b) is added to 1 ml of medium at the beginning of or at some midpoint of the culture. It is desired that compound (I-a) or compound (I-b) is added after it is dissolved in an organic solvent such as methyl alcohol or ethyl alcohol.

In a case where a method of allowing an enzyme source obtained by culturing cells to act upon compound (I-a) or compound (I-b) in an aqueous medium, the amount of enzyme to be used depends on the specific activity of the enzyme source or the like. For example, when a culture of cells, cells, or a treated product thereof is used as an enzyme source, 5 to 1,000 mg, preferably 10 to 400 mg of enzyme source is added per 1 mg of compound (I-a) or compound (I-b). The reaction is performed in an aqueous medium preferably at 20 to 50° C., and particularly preferably at 25 to 37° C. The reaction period depends on the amount, specific activity and the like of an enzyme source to be used, and it is usually 2 to 150 hours, preferably 6 to 120 hours.

Examples of an aqueous medium include water, or buffers such as phosphate buffer, HEPES (N-2 hydroxyethylpiperazine-N-ethanesulfonate) buffer and Tris (tris(hydroxymethyl)aminomethane)hydrochloride buffer. An organic solvent may be added to the above buffers, unless it inhibits reaction. Examples of organic solvent include acetone, ethyl acetate, dimethyl sulfoxide, xylene, methyl alcohol, ethyl alcohol and butanol. A mixture of an organic solvent and an aqueous medium is preferably used, for example when compound (I-b) is used.

In the case where compound (I-a) or compound (I-b) is added to the aqueous medium, compound (I-a) or compound (I-b) is dissolved in an aqueous medium capable of dissolving compound (I-a) or compound (I-b), and then is added to the medium. An organic solvent may be added to the above buffers, unless it inhibits reaction. Examples of organic solvents include acetone, ethyl acetate, dimethyl sulfoxide, xylene, methyl alcohol, ethyl alcohol and butanol.

Compound (I-b) and compound (II-b) can easily be converted into compound (I-a) and compound (II-a) respectively by a method for opening a lactone ring as mentioned below. Likewise, compound (I-a) and compound (II-a) can easily be converted into compound (I-b) and compound (II-b) respectively by a method for producing lactone as mentioned below.

Examples of a method for opening a lactone ring include a method which comprises dissolving compound (I-b) or compound (II-b) in an aqueous medium and adding thereto an acid or alkali. Examples of the aqueous medium include water and an aqueous solution containing salts, which does not inhibit the reaction, such as phosphate buffer, Tris buffer and the like. The above aqueous solution may contain an organic solvent such as methanol, ethanol, ethyl acetate and the like in a concentration which does not inhibit the reaction. Examples of acid include acetic acid, hydrochloric acid and sulfuric acid, and examples of alkali include sodium hydroxide, potassium hydroxide and ammonia.

Examples of a method for producing lactone include a method which comprises dissolving compound (I-a) or compound (II-a) in a non-aqueous solvent and adding thereto an acid or base catalyst. As long as the non-aqueous solvent is an organic solvent which does not substantially contain water and can dissolve compound (I-a) or compound (II-a), any type of non-aqueous solvent can be used. Examples of non-aqueous solvents include dichloromethane and ethyl acetate. As a catalyst, any catalyst can be used, as long as it catalyzes lactonization and does not show any actions other than lactonization on a substrate or a reaction product. Examples of the above catalyst include trifluoroacetic acid and para-toluenesulfonic acid. Reaction temperature is not particularly limited, but is preferably 0 to 100° C., and is more preferably 20 to 80° C.

The collection of compound (II-a) or compound (II-b) from the reaction solution can be carried out by any ordinary methods used in the field of organic synthetic chemistry such as extraction with organic solvents, crystallization, thin-layer chromatography, high performance liquid chromatography, and the like.

As a method for detecting and quantifying compound (II-a) or compound (II-b) obtained by the present invention, any method can be used, as long as the detection or quantification of compound (II-a) and/or compound (II-b) can be performed. Examples thereof include $^{13}$C-NMR spectroscopy, $^1$H-NMR spectroscopy, mass spectroscopy and high performance liquid chromatography (HPLC).

In the present invention, some compounds of compound (I-a), compound (I-b), compound (II-a) and compound (II-b) can have stereoisomers such as optical isomers. The present invention covers all possible isomers and mixtures thereof including these stereoisomers.

As compound (I-a), compound (III-a) is preferable, compound (V-a) is more preferable, and compound (VII-a) is particularly preferable.

As compound (I-b), compound (II-b) is preferable, compound (V-b) is more preferable, and compound (VII-b) is particularly preferable.

As compound (II-a), compound (IV-a) is preferable, compound (VI-a) is more preferable, and compound (VIII-a) is particularly preferable.

As compound (II-b), compound (IV-b) is preferable, compound (VI-b) is more preferable, and compound (VIII-b) is particularly preferable.

Alkyl is a linear or branched alkyl containing 1 to 10 carbon atoms, preferably 1 to 6 carbon atoms, such as methyl, ethyl, propyl, isopropyl, butyl, isobutyl, sec-butyl, tert-butyl, pentyl, neopentyl, hexyl, isohexyl, heptyl, 4,4-dimethylpentyl, octyl, 2,2,4-trimethylpentyl, nonyl, decyl, and various branched chain isomers thereof.

Examples of aryl include phenyl and naphthyl.

The substituent in the substituted alkyl may be 1 to 3 identical or different groups, and examples thereof include halogens, hydroxy, amino, alkoxy and aryl.

The substituent in the substituted aryl may be 1 to 3 identical or different groups, and examples thereof include halogens, hydroxy, amino, alkyl and alkoxy.

The alkyl moiety in alkoxy has the same definition as in the alkyl mentioned above.

Alkali metal represents each element of lithium, sodium, potassium, rubidium, cesium or francium.

The examples of the present invention is described below, but the present invention is not limited to these examples.

BEST MODE FOR CARRYING-OUT OF THE INVENTION

EXAMPLE 1

Obtaining of the DNA Encoding the Protein having an Activity of Producing Compound (VIII-a) or Compound (VIII-b) from Compound (VII-a) or Compound (VII-b)

100 mg of compound (VII-b) (produced by Sigma) was dissolved in 9.5 ml of methanol, and 0.5 ml of 1 mol/l sodium hydroxide was added. The mixture was stirred at room temperature for 1 hour. The obtained reaction solution was dried to be solidified, and was dissolved by adding 5 ml of deionized water, followed by adjusting pH to about 7 with about 0.1 ml of 1 mol/l hydrochloric acid. Then, 4.9 ml of deionized water was added to the mixture to obtain 10 ml of compound (VII-a), whose final concentration was 10 mg/ml (a compound wherein, in formula (VII-a), $R^1$ is sodium).

*Bacillus subtilis* Marburg168 strain (ATCC15563) was inoculated with 1 platinum loop in a 10 ml LB liquid medium, and cultured at 30° C. overnight. After culturing, cells were collected from the obtained culture solution by centrifugation.

A chromosomal DNA was isolated and purified from the cells in a usual manner.

Sense and antisense primers having a combination of nucleotide sequences: SEQ ID NOS: 3 and 4, SEQ ID NOS: 5 and 6, SEQ ID NOS: 7 and 8, SEQ ID NOS: 9 and 10, SEQ ID NOS: 11 and 12, SEQ ID NOS: 13 and 14, and SEQ ID NOS: 15 and 16, were synthesized with a DNA synthesizer.

Using the chromosomal DNA as a template, PCR was performed with these primers and with TaKaRa LA-PCR™ Kit Ver.2 (produced by TAKARA), Expand™ High-Fidelity PCR System (produced by Boehringer Mannheim) or Taq DNA polymerase (produced by Boelinnger) using a DNA Thermal Cycler (produced by Perkin-Elmer Japan).

PCR was performed for 30 cycles in which each cycle consists of reaction steps of 30 seconds at 94° C., 30 seconds at 55° C. and 2 minutes at 72° C. for DNA fragments of 2 kb or less; and 20 seconds at 98° C., 3 minutes at 68° C. for DNA fragments of more than 2 kb, and then reaction was carried out for 7 min at 72° C.

Among DNA fragments amplified by PCR, the DNA fragment (containing biol gene) amplified by a combination of primers of SEQ ID NOS:3 and 4 was digested with restriction enzymes EcoRI and SalI, DNA fragment (containing cypA gene) amplified by a combination of primers of SEQ ID NOS:5 and 6 was digested with XbaI and SmaI, DNA fragment (containing cypX gene) amplified by a combination of primers of SEQ ID NOS:7 and 8 was digested with SmaI and SalI, DNA fragment (containing pksS gene) amplified by a combination of primers of SEQ ID NOS:9 and 10 was digested with EcoRI and SalI, DNA fragment (containing yet0 gene) amplified by a combination of primers of SEQ ID NOS:11 and 12 was digested with XbaI and BglII, DNA fragment (containing yjiB gene) amplified by a combination of primers of SEQ ID NOS:13 and 14 was digested with XbaI and SmaI, and DNA fragment (containing yrhJ gene) amplified by a combination of primers of SEQ ID NOS:15 and 16 was digested with XbaI and SmaI, respectively.

After digestion, the DNA fragments treated with the restriction enzymes were subjected to agarose gel electrophoresis to obtain the DNA fragments treated with various restriction enzymes.

A vector plasmid pUC119 (produced by TAKARA) was digested with restriction enzymes SalI and EcoRI, then subjected to agarose gel electrophoresis to obtain a SalI-EcoRI treated pUC119 fragment. Similarly, a vector plasmid pUC119 was digested with restriction enzymes SalI and SmaI, then subjected to agarose gel electrophoresis to obtain a SalI-SmaI treated pUC119 fragment.

pSTV28 (produced by TAKARA) was digested with restriction enzymes XbaI and SmaI, then subjected to agarose gel electrophoresis to obtain a XbaI-SmaI treated pSTV28 fragment. Similarly, a vector plasmid pSTV28 was digested with restriction enzymes XbaI and BamHI, then subjected to agarose gel electrophoresis to obtain a XbaI-BamHI treated pSTV28 fragment.

The thus-obtained EcoRI-SalI treated DNA fragment (amplified by PCR with a combination of primers of SEQ ID NOS:3 and 4) was mixed with the SalI-EcoRI treated pUC119 fragment, XbaI-SmaI treated DNA fragment (amplified by PCR with a combination of primers of SEQ ID NOS:5 and 6) was mixed with the XbaI-SmaI treated pSTV28 fragment, SmaI-SalI treated DNA fragment (amplified by PCR with a combination of primers of SEQ ID NOS:7 and 8) was mixed with the SalI-SmaI treated pUC119 fragment, EcoRI-SalI treated DNA fragment (amplified by PCR with a combination of primers of SEQ ID NOS:9 and 10) was mixed with the SalI-EcoRI treated pUC119 fragment, XbaI-BglII treated DNA fragment (amplified by PCR with a combination of primers of SEQ ID NOS:11 and 12) was mixed with the XbaI-BamHI treated pSTV28 fragment, XbaI-SmaI treated DNA fragment (amplified by PCR with a combination of primers of SEQ ID NOS:13 and 14) was mixed with the XbaI-SmaI treated pSTV28 fragment, XbaI-SmaI treated DNA fragment (amplified by PCR with a combination of primers of SEQ ID NOS:15 and 16) was mixed with XbaI-SmaI treated pSTV28 fragment, respectively. After ethanol precipitation, the obtained DNA precipitates were dissolved in 5 µl of distilled water, and a ligation reaction was carried out to obtain each recombinant DNA.

Using the recombinant DNA, E. coli (purchased from TOYOBO) DH5 α strain is transformed by a usual method, then the transformant was plated to a LB agar medium [containing Bacto Trypton (produced by Difco) 10 g, Bactoyeast extract (produced by Difco) 5 g, NaCl 5 g in 1 L; and adjusted to pH7.4 with 1 mol/l NaOH such that the agar is adjusted to 1.5%] containing 100 µg/ml ampicillin in the case where the pUC119 is used as a vector plasmid; and to a LB agar medium containing 25 µg/ml chloramphenicol in the case where the pSTV28 is used as a vector plasmid, followed by culturing for 2 days at 25° C.

Several colonies of the grown ampicillin-resistant or chloramphenicol-resistant transformants were selected, inoculated in 10 ml LB liquid medium [which contains Bacto Trypton (produced by Difco) 10 g, Bactoyeast extract (produced by Difco) 10 g and NaCl 5 g in 1 L; and is adjusted to pH 7.4 with 1 mol/l NaOH], and then cultured while shaking for 2 days at 25° C.

The obtained culture was centrifuged to recover cells.

A plasmid was isolated from the cells in a usual manner.

The structure of the isolated plasmid was examined by cleaving it with various restriction enzymes and the nucleotide sequences were determined, thereby confirming that the desired DNA fragment was inserted in the plasmid. The plasmids obtained by linking the DNA fragment (amplified by PCR with a combination of primers of SEQ ID NOS:3 and 4) treated with EcoRI-SalI to pUC119 fragment treated with SalI-EcoRI, was named pUbioI, the plasmids obtained by linking DNA fragment (amplified by PCR with a combination of primers of SEQ ID NOS:5 and 6) treated with XbaI-SmaI to pSTV28 fragment treated with XbaI-SmaI was named pScypA, the plasmids obtained by linking DNA fragment (amplified by PCR with a combination of primers of SEQ ID NOS:7 and 8) treated with SmaI-SalI to pUC119 fragment treated with SalI-SmaI was named pUcypX, the plasmids obtained by linking DNA fragment (amplified by PCR with a combination of primers of SEQ ID NOS:9 and 10) treated with EcoRI-SalI to pUC119 fragment treated with SalI-EcoRI was named pUpksS, the plasmids obtained by linking DNA fragment (amplified by PCR with a combination of primers of SEQ ID NOS:11 and 12) treated with XbaI-BglII to pSTV28 fragment treated with XbaI-BamHI was named pSyetO, the plasmids obtained by linking DNA fragment (amplified by PCR with a combination of primers of SEQ ID NOS:13 and 14) treated with XbaI-SmaI to pSTV28 fragment treated with XbaI-SmaI was named pSyjiB, the plasmids obtained by linking DNA fragment (amplified by PCR with a combination of primers of SEQ ID NOS:15 and 16) treated with XbaI-SmaI to pSTV28 fragment treated with XbaI-SmaI was named pSyrhJ, respectively.

E. coli DH5 α containing the thus-obtained plasmid, E. coli DH5 α containing pUC119 or pSTV28, and E. coli DH5 α containing no plasmid were inoculated respectively in 3 ml of LB liquid medium (to which a drug which corresponds to a drug-resistant gene in a vector plasmid was added) and cultured while shaking for 12 hours at 28° C. The culture solution (0.5 ml) was inoculated to a LB liquid medium (to which a drug which corresponds to a drug-resistant gene was added) containing 1% glucose and 1% $CaCO_3$, and was cultured while shaking for 12 hours at 28° C. The culture solution (1 ml) was poured into an assist tube (produced by ASSIST), then glucose and the previously obtained compound (VII-a) (wherein $R^1$ is a Na) were added to a final concentration of 1% and 100 mg/l, respectively, followed by shaking for 24 hours at 28° C. Upon completion of the reaction, cells were removed by centrifugation, then the obtained supernatant was thoroughly shaken with addition of the same amount of ethyl acetate. The upper ethyl acetate layer was separated from the solution by centrifugation, then the ethyl acetate layer was evaporated to dryness by a centrifugal evaporator. The dried matter was dissolved in one-fifths volume of methanol relative to that of the first culture supernatant, and subjected to a HPLC analysis [column; Inertsil ODS-2 (5 µm, 4×250 mm, manufactured by GL science), column temperature; 60° C., mobile phase; acetonitrile: water: phosphoric acid=55:45:0.05, flow rate: 0.9 ml/min, detection wavelength: 237 nm] to detect and quantify the compound (VIII-a) (wherein $R^1$ is Na). The results are shown in Table 1.

TABLE 1

| Plasmid | Compound (VIII-a) (mg/l) |
|---|---|
| None | 0 |
| pUC119 | 0 |
| pSTV28 | 0 |
| pUbioI | 0 |
| pScypA | 0 |
| pUcypX | 0 |
| pUpksS | 0 |
| pSyetO | 0 |
| pSyjiB | 0.6 |
| pSyrhJ | 0 |

EXAMPLE 2

Expression of yjiB Gene in *Bacillus subtilis* as a Host Cell and Confirmation of Activity of the Protein Encoded by Said Gene Sense and antisense primers having a combination of nucleotide sequences shown by SEQ ID NOS:17 and 18, SEQ ID NOS:19 and 20, SEQ ID NOS:21 and 22, SEQ ID NOS:23 and 24, SEQ ID NOS:25 and 26, SEQ ID NOS:27 and 28, and SEQ ID NOS:29 and 30, were synthesized with a DNA synthesizer.

Using the chromosomal DNA of *Bacillus subtilis* obtained in Example 1 as a template, PCR was performed with these primers and with TaKaRa LA-PCR™ Kit Ver.2 (produced by TAKARA), Expand™ High-FidelityPCR System (produced by Boehringer Mannheim) or Taq DNA polymerase (produced by Boellinnger) using a DNA Thermal Cycler (produced by Perkin-Elmer Japan).

PCR was performed for 30 cycles under the conditions where one cycle consists of the reaction steps of 30 seconds at 94° C., 30 seconds at 55° C. and 2 minutes at 72° C. for the DNA fragments of 2 kb or less, and 20 seconds at 98° C. and 3 minutes at 68° C. for the DNA fragments of more than 2 kb, and then a reaction was carried out for 7 minutes at 72° C.

Among DNA fragments amplified by PCR, the DNA fragment (containing biol gene) amplified by a combination of primers of SEQ ID NOS:17 and 18 was digested with rectriction enzymes SpeI and BamHI, DNA fragment (containing cypA gene) amplified by a combination of primers of SEQ ID NOS:19 and 20 was digested with SpeI and BamHI, DNA fragment (containing cypX gene) amplified by a combination of primers of SEQ ID NOS:21 and 22 was digested with SpeI and NruI, DNA fragment (containing pksS gene) amplified by a combination of primers of SEQ ID NOS:23 and 24 was digested with SpeI and BamHI, DNA fragment (containing yet0 gene) amplified by a combination of primers of SEQ ID NOS:25 and 26 was digested with SpeI and BamHI, DNA fragment (containing yjiB gene) amplified by a combination of primers of SEQ ID NOS:27 and 28 was digested with SpeI and BamHI, DNA fragment (containing yrhJ gene) amplified by a combination of primers of SEQ ID NOS:29 and 30 was digested with SpeI and BamHI, respectively.

After digestion, the DNA fragments treated with the restriction enzymes were subjected to agarose gel electrophoresis to obtain the DNA fragments treated with each restriction enzyme.

A vector plasmid pWH1520 (produced by MoBiTec) was digested with restriction enzymes SpeI and BamHI, then subjected to agarose gel electrophoresis to obtain a SpeI-BamHI treated pWH1520 fragment. Similarly, a vector plasmid pWH1520 was digested with restriction enzymes SpeI and NruI, then subjected to agarose gel electrophoresis to obtain a SpeI-NruI pWH1520 fragment.

The thus-obtained SpeI-BamHI treated DNA fragments (amplified by PCR with a combination of primers of SEQ ID NOS:17 and 18, SEQ ID NOS:19 and 20, SEQ ID NOS:23 and 24, SEQ ID NOS:25 and 26, SEQ ID NOS:27 and 28, and SEQ ID NOS:29 and 30) were mixed with the SpeI-BamHI treated pWF1520 fragment; SpeI-NruI treated DNA fragment (amplified by PCR with a combination of primers of SEQ ID NOS:21 and 22) was mixed with SpeI-NruI pWF1520 fragment, respectively. After ethanol precipitation, the obtained DNA precipitates were dissolved in 5 µl of distilled water, and a ligation reaction was carried out to obtain each recombinant DNA.

Using the recombinant DNA, *E. coli* (purchased from TOYOBO) DH5 α strain was transformed by a usual method, then plated to a LB agar medium containing 10 µg/ml of tetracycline, and cultured for 2 days at 25° C. Cells were recovered from the obtained culture by centrifugation.

A plasmid was isolated from the cells in a usual manner.

The structure of the isolated plasmid was examined by cleaving it with various restriction enzymes and the nucleotide sequences thereof were determined, thereby confirming that the desired DNA fragment was inserted in the plasmid. The plasmid obtained by linking the DNA fragment amplified by PCR with a combination of primers of SEQ ID NOS:17 and 18 to pWH1520 was named as pWbioI; the plasmid obtained by linking the DNA fragment amplified by PCR with a combination of primers of SEQ ID NOS:19 and 20 to pWH1520 was named as pWcypA; the plasmid obtained by linking the DNA fragment amplified by PCR with a combination of primers of SEQ ID NOS:21 and 22 to pWH1520 was named as pWcypX; the plasmid obtained by linking the DNA fragment amplified by PCR with a combination of primers of SEQ ID NOS:23 and 24 to pWH1520 was named as pWpksS; the plasmid obtained by linking the DNA fragment amplified by PCR with a combination of primers of SEQ ID NOS:25 and 26 to pWH1520 was named as pWyet0; the plasmid obtained by linking the DNA fragment amplified by PCR with a combination of primers of SEQ ID NOS:27 and 28 to pWH1520 was named as pWyjiB; the plasmid obtained by linking the DNA fragment amplified by PCR with a combination of primers of SEQ ID NOS:29 and 30 to pWH1520 was named as pWyrhJ, respectively.

The thus-obtained plasmids and the vector plasmid pWH1520 were introduced in a *Bacillus subtilis* ATCC33712 strain according to the method by S. chang and S. N. cohen [S. chang and S. N. cohen: Mol. Gen. Genet., 168, 111 (1979).]

That is, ATCC33712 strain was inoculated in a thick tube containing 5 ml of Pen medium (where 1.75 g of Difco Antibiotic medium No. 3 was dissolved in 100 ml of water and sterilized in an autoclave), then cultured with shaking at 37° C. overnight. Total cells cultured overnight in 300 ml Erlenmeyer flask containing 100 ml of Pen medium were then inoculated and cultured with shaking for 3 hours at 37° C. to be grown until reaching a metaphase of exponential growth. The culture was centrifuged for 10 minutes at 5000 rpm in germ-free conditions to precipitate the cells. After removing the supernatant, the cells were suspended in 4.5 ml of SMMP [mixture comprising equal amount of 2×SMMP (where sucrose 34.2 g, maleic acid 0.464 g, magnesium chloride.6H$_2$O 0.813 g were dissolved in water, which was adjusted to pH6.5 with sodium hydroxide, then the final volume of 100 ml was sterilized in an autoclave) and 4×Pen medium (where 7 g of Difco Antibiotic medium No. 3 was dissolved in 100 ml of water and sterilized in an autoclave)], followed by addition of 0.5 ml of lysozyme solution [where 10 mg of lysozyme (produced by EIKAGAKU corp.) was dissolved in 0.5 ml of SMMP, and sterilized with a millipore filter having a pore size of 0.45 µm], and the mixture was slowly shaken for 2 hours at 37° C. After microscopically confirming that not less than 90% cells became protoplast, the protoplasts were centrifuged for 20 minutes at 3000 rpm to be precipitated. The supernatant was removed, and the obtained protoplasts were resuspended in 5 ml of SMMP. The protoplasts were collected by centrifugation for 20 minutes at 3000 rpm, and suspended in 2 ml of SMMP to prepare a protoplast suspension of a recipient strain for transformation.

Approximately 1 μg of plasmid DNA was dissolved in SMMP, and thoroughly mixed with 0.5 ml of protoplast suspension. Immediately after mixing, 1.5 ml of 40% polyethylene glycol solution [where 40 g of polyethylene glycol 6000 (Nacalai tesque) was dissolved in 2×SMMP, and water was added thereto to become the volume of 100 ml, followed by sterilization in an autoclave] was added thereto and thoroughly mixed. After standing at room temperature for 2 minutes, 5 ml of SMMP was added and mixed, and the mixture was centrifuged for 20 minutes at 3000 rpm. After removing the supernatant, the precipitated protoplasts were suspended in 1 ml of SMMP, then slowly shaken for 3 hours at 30° C. After dilution with SMMP as appropriate, the protoplasts were applied to a DM3 medium [in which 45 ml of 80 g/L bactoagar (produced by Difco), 50 ml of 50 g/L casamino acid, 250 ml of 338 g/L sodium succinate .6$H_2O$ (pH7.3), 50 ml phosphate buffer (35 g/L potassium hydrogen phosphate, 15 g/L potassium dihydrogen phosphate), 25 ml of 100 g/L yeast extract, 10 ml of 203 g/L magnesium chloride.6$H_2O$, 25 ml of 100 g/L glucose were respectively sterilized in an autoclave and mixed, then 3.5 ml of 20 mg/ml bovine serum albumin sterilized with millipore filter having a pore size of 0.45 μm was added thereto] wherein the medium containing drugs (in case of tetracycline, it was added to the final volume of 10 μg/ml). The protoplasts were cultured for 1 to 2 days at 37° C. to obtain the transfected strain.

Thus, B. subtilis ATCC33712 strains having each of the above plasmids were obtained.

The obtained transformants and ATCC33712 strain having no plasmid were inoculated respectively in 3 ml LB liquid media (wherein 10 mg/l tetracycline was added to a plasmid-containing strain), and cultured with shaking for 24 hours at 30° C. 0.25 ml of this culture solution was inoculated in a test tube containing a 5 ml of TB medium [Bacto Trypton (produced by Difco) 1.4%, Bacto yeast extract (produced by Difco) 2.4%, $KH_2PO_4O$ 0.231%, and $K_2HPO_4$ 1.251%, adjusted to pH7.4 with 1 mol/l sodium hydroxide], and cultured with shaking for 3 hours at 30° C. After 3 hours, 1 ml of the culture was transferred to an assist tube No. 60.540S (produced by ASSIST) and 40 μl of 50% sterilized xylose solution was added thereto, followed by culturing with shaking for 3 hours. Then, the compound (VII-a) (wherein R is Na) obtained in Example 1 was added to each test tube to the final concentration of 0.2 mg/ml, and the mixture was cultured whith shaking for 16 hours at 30° C.

Upon completion of reaction, the reaction solution was adjusted to pH 3.5 with acetic acid. 1 ml of ethyl acetate was added to 0.5 ml of this reaction solution, and the mixture was shaken for 1 hour. After shaking, the reaction solution was centrifuged for 5 minutes at 3000 rpm to be separated into 2 layers, and the upper ethyl acetate layer was recovered, the solvent was removed by a centrifugal evaporator, and the residue was dissolved in 0.5 ml of methanol.

Using an aliquot of this methanol solution, HPLC analysis was performed as in Example 1 to detect and quantify compound (VIII-a) (wherein $R^1$ is Na). The results are shown in Table 2.

TABLE 2

| Plasmid | Compound (VIII-a) (mg/l) |
| --- | --- |
| None | 0.5 |
| pWH1520 | 0.5 |
| pWbioI | 0.5 |
| pWcypA | 0.5 |
| pWcypX | 0.5 |
| pWpksS | 0.5 |
| pWyetO | 0.5 |
| pWyjiB | 24.6 |
| pWyrhJ | 0.5 |

As seen from the results of Example 1 and 2, it is obvious that activity of producing compound (VIII-a) or compound (VIII-b) from compound (VII-a) or compound (VII-b) is encoded by yjiB gene.

The DNA fragment amplified by PCR with a combination of primers of SEQ ID NO:27 and 28 above, contained the nucleotide sequence shown by SEQ ID NO:2; and said nucleotide sequence contained a nucleotide sequence encoding a protein having the amino acid sequence shown by SEQ ID NO:1.

EXAMPLE 3

Expression of yjiB Gene Using Bacillus megaterium as a Host Cell and Production of Compound (VIII-a)

pWyjiB prepared in Example 2 was introduced into Bacillus megaterium (produced by MoBiTec) and Bacillus sp. FERM BP-6030 in the same manner as is described for transformation of Bacillus subtilis in Example 2.

The obtained transformant and a host cell having no plasmid were cultured and reaction was carried out in the same manner as in Example 2, and the amount of produced compound (VIII-a) was measured. The results are shown in Table 3.

TABLE 3

| Host | Plasmid | Compound (VIII-a) (mg/l) |
| --- | --- | --- |
| B. megaterium | none | 2.0 |
| (as above) | pWyjiB | 27.2 |
| FERM BP-6030 | none | 4.5 |
| (as above) | pWyjiB | 30.3 |

EXAMPLE 4

Preparation of the Plasmid for Expressing the Protein which Produces Compound (VIII-a) in Coryne-Form Bacteria To allow efficient expression of yjiB gene obtained in Example 1 in coryne-form bacteria, DNAs having nucleotide sequences shown by SEQ ID NOS:31, 32, 33, 34, 35, 36, 37, 38 and 39 were synthesized with a DNA synthesizer.

The plasmid pR1109 DNA in which the DNA fragment comprising a promoter sequence p54-6 (GenBank AJ132582) for expression in coryne-form bacteria and having the nucleotide sequence shown by SEQ ID NO:40 was inserted into a Sse83871-BamHI site of a plasmid vector pCS299P (Japanese Patent Application No. 11-110437), was prepared in a usual manner from E. coli NM522 strain transformed with this plasmid.

Using pWyjiB DNA obtained in Example 2 as a template, PCR was performed with DNA primers having nucleotide sequences shown by SEQ ID NOS:31 and 32 and with Taq DNA polymerase (produced by TAKARA) using a DNA Thermal Cycler 480 (produced by Perkin-Elmer Japan).

PCR was performed for 25 cycles in which each cycle consists of reaction steps of 30 seconds at 96° C., 45 seconds at 50° C. and 3 minutes at 72° C.

DNA fragment amplified by PCR was digested with SalI and BamHI and subjected to agarose gel electrophoresis, and an approximately 1.2 kb DNA fragment was purified in a usual manner to obtain a SalI-BamHI treated DNA fragment.

The above-obtained plasmid pRI109 DNA was digested with restriction enzymes SalI and BamHI and subjected to agarose gel electrophoresis, and an approximately 6 kb DNA fragment was purified in a usual manner to obtain a SalI-BamHI treated pRI109 fragment.

The above-obtained SalI-BamHI treated DNA fragment and SalI-BamHI treated pRI109 fragment were mixed, and ligation reaction was carried out to obtain the recombinant DNA.

Using the recombinant DNA, E. coli DH5 α(purchased from TOYOBO) was transformed by a usual method, then plated to a LB agar medium containing 20 µg/ml kanamycin and cultured for 1 day at 30° C. to obtain the transformant.

A plasmid was isolated from the transformant in a usual manner. Using the isolated plasmid DNA as a template, and using DNAs having nucleotide sequences shown by SEQ ID NOS:33, 34, 35, 36 and 37 as primers respectively, the nucleotide sequences of the inserted DNA fragments were determined with a DyeTerminator Cycle Sequencing Kit (produced by Applied Biosystem) and 373A sequencer (produced by Applied Biosystem), then the plasmid in which the nucleotide sequence shown by SEQ ID NO:41 was inserted between SalI and BamHI sites of pRI109 was named pRIyjiB.

The nucleotide sequence shown by SEQ ID NO:41 contained the nucleotide sequence which encoded the protein having the amino acid sequence shown by SEQ ID NO:42.

Using the chromosomal DNA of Bacillus subtilis Marburg168 strain (ATCC15563) obtained in Example 1 as a template, PCR was performed with DNA primers having nucleotide sequences shown by SEQ ID NOS:38 and 39, and with LA-Taq DNA polymerase (produced by TAKARA) using a DNA Thermal Cycler 480 (produced by Perkin-Elmer Japan).

PCR was performed for 30 cycles in which each cycle consists of reaction steps of 30 seconds at 96° C., 30 seconds at 55° C. and 2 minutes at 72° C., and then a reaction was carried out for 7 minutes at 72° C.

The DNA fragment amplified by PCR was mixed with pT7Blue (produced by TAKARA), and ligation reaction was carried out to obtain the recombinant DNA.

Using the recombinant DNA, E. coli DH5 α (purchased from TOYOBO) was transformed by a usual method, then plated to a LB agar medium containing 100 µg/ml ampicillin and cultured for 1 day at 30° C. to obtain the transformant.

A plasmid was isolated from the transformant by a usual method. The structure of the isolated plasmid was examined by cleaving it with various restriction enzymes, thereby confirming that the desired DNA fragment was inserted in the plasmid, and the plasmid was named as pTSYN2-72.

The pTSYN2-72 DNA was digested with XhoI and BamHI and subjected to agarose gel electrophoresis, and then an approximately 1.2 kb DNA fragment was purified by a usual method to obtain a XhoI-BamHI treated DNA fragment.

The plasmid pRI109 DNA was digested with restriction enzymes SalI and BamHI and subjected to agarose gel electrophoresis, and then an approximately 6 kb DNA fragment was purified by a usual method to obtain a SalI-BamHI treated pRI109 fragment.

The above-obtained XhoI-BamHI treated DNA fragment and SalI-BamHI treated pRI109 fragment were mixed, and the ligation reaction was carried out to obtain the recombinant DNA.

Using the recombinant DNA, E. coli DH5 α (purchased from TOYOBO) was transformed by a usual method, then plated to a LB agar medium containing 20 µg/ml kanamycin and cultured for 1 day at 30° C. to obtain a transformant.

A plasmid was isolated from the transformant by a usual method. Using the isolated plasmid DNA as a template, and using DNAs having nucleotide sequences shown by SEQ ID NOS:33, 34, 35, 36 and 37, the nucleotide sequences of the inserted DNA fragment were determined with a DyeTerminator Cycle Sequencing Kit (produced by Applied Biosystem) and 373A sequencer (produced by Applied Biosystem), and the plasmid in which the nucleotide sequence shown by SEQ ID NO:43 was inserted between SalI-BamHI site of pRI109, was named pSYN2-72.

The nucleotide sequence shown by SEQ ID NO:43 contained the nucleotide sequence which encodes the protein having the amino acid sequence shown by SEQ ID NO:1.

Using pWyjiB DNA obtained in Example 2 as a template, PCR was performed with DNA primers having nucleotide sequences shown by SEQ ID NO:38 and 39, and with Z-Taq DNA polymerase (produced by TAKARA) using a DNA Thermal Cycler 480 (produced by Perkin-Elmer Japan).

PCR was performed for 25 cycles in which each cycle consists of reaction steps of 20 seconds at 98° C., 20 seconds at 55° C. and 30 minutes at 72° C.

The DNA fragment amplified by PCR was digested with XhoI and BamHI and subjected to agarose gel electrophoresis, and then an approximately 1.2 kb DNA fragment was purified by a usual method to obtain a XhoI-BamHI treated DNA fragment.

The plasmid pRI109 DNA was digested with restriction enzymes SalI and *BamHI and subjected to agarose gel electrophoresis, then an approximately* 6 kb DNA fragment was purified by a usual method to obtain a SalI-BamHI treated pRI109 fragment.

The above-obtained XhoI-BamHI treated DNA fragment and SalI-BamHI treated pRI109 fragment were mixed, and ligation reaction was carried out to obtain the recombinant DNA.

Using the recombinant DNA, E. coli DH5 α (purchased from TOYOBO) was transformed by a usual method, then plated to a LB agar medium containing 20 µg/ml kanamycin and cultured for 1 day at 30° C. to obtain the transformant.

A plasmid was isolated from the transformant by a usual method. Using the isolated plasmid DNA as a template, and using DNAs having nucleotide sequences shown by SEQ ID NOS:33, 34, 35, 36 and 37 respectively as primers, the nucleotide sequences of the inserted DNA fragments were determined with a DyeTerminator Cycle Sequencing Kit (produced by Applied Biosystem) and 373A sequencer (produced by Applied Biosystem), and the plasmid in which the nucleotide sequence shown by SEQ ID NO:44 was inserted between SalI-BamHI site of pRI109, was named pSYN2-39.

The nucleotide sequence shown by SEQ ID NO:44 contained the nucleotide sequence which encodes the protein having the amino acid sequence shown by SEQ ID NO:45.

EXAMPLE 5

Introduction of the Plasmid into the C. glutamicum ATCC13032 Strain and Evaluation of Activity ATCC13032 strain was inoculated in a test tube containing 8 ml of broth medium [20 g/l normal broth medium (produced by Kyokuto Pharmaceutical Industry, Co. Ltd), 5 g/l Bacto Yeast Extract (produced by Difco)] and cultured with shaking 30° C. overnight. Subsequently, 5 ml of cells cultured overnight were inoculated in a 2 L Erienmeyer flask (bearing a buffle(s)) containing 250 ml of broth medium and cultured with shaking for 4 hours at 30° C. The obtained culture solution was centrifuged to precipitate the cells. After removing the supernatant, the cells were suspended in 30 ml of ice-cold EPB [250 mmol/l Sucrose, 15% (v/v) glycerol], and centrifuged to be precipitated. Similarly, the cells were resuspended in EPB and centrifuged to be separated, and then the cells were suspended in 2 ml of EPB. The obtained cell suspension was poured into 0.5 ml tubes by 0.1 ml each, and was quickly frozen with dry ice to obtain the cell suspension for transformation. The obtained cells were stored at a temperature below −80° C.

0.1 ml of the frozen cell suspension for transformation was dissolved on ice, retained for 10 minutes at 43.5° C., and transferred onto ice. After 2 µl of aqueous solution containing approximately 2 µg pRI109 DNA was added, the cell suspension was transferred to the previously iced E. coli GenePulser cuvet (produced by BioRad), and then the DNA was introduced into cells under conditions of 25 µF, 200Ω and 1.5 kV by electroporation using GenePulser (produced by BioRad). Immediately after electroporation, total amount of the cell suspension was moved to a 15 ml-test tube containing 1 ml of broth medium, and cultured with shaking for 1 hour at 30° C.

The obtained culture solution was centrifuged for 10 minutes at 3,500 rpm to precipitate the cells. After removing the supernatant, the cells were suspended with addition of 0.1 ml broth medium, then the suspension was applied to a broth agar medium [which was solidified with 2% Difco Agar] containing 20 µg/ml kanamycin and cultured for 2 days at 30° C. to obtain the transformant.

Thus, C. glutamicum ATCC13032 strain having pRI109 was obtained.

As in the above, C. glutamicum ATCC13032 strains having each plasmid, pRIyjiB, pSYN2-72, pSYN2-39 were obtained.

The obtained transformants were inoculated in test tubes which contain 3 ml of broth media containing 100 µg/ml kanamycin, and cultured with shaking for 24 hours at 30° C. The culture (0.2 ml) was inoculated in a test tube containing 2 ml of LMC medium [in which separately sterilized Glucose, $MgSO_4$, $FeSO_4$, $MnSO_4$ were added to a pre-LMC medium sterilized in a autoclave ($NH_4Cl$ 1 g/l, $KH_2PO_4$ 1 g/l, $K_2HPO_4$ 3 g/l, Difco Yeast Extract 0.2 g/l, Urea 1 g/l, Biotin 0.05 mg/l, Thiamin 0.5 mg/l, Corn Steep Liquor 10 g/l; pH7.2) to the final concentration of 30 g/l, 0.1 g/l, 2 mg/l and 2 mg/l, respectively] wherein the medium contains 100 µg/ml kanamycin, and cultured with shaking for 5 hours at 30° C. The compound (VII-a) (wherein R is Na) was added thereto to the final concentration of 300 mg/l, and the mixture was reacted with shaking for 16 hours at 30° C.

0.5 ml of the reaction solution was moved to a 1.5 ml tube, and centrifuged for 2 minutes at 15,000 rpm to separate the cells. The obtained supernatant was diluted 5 to 20 times with methanol and centrifuged for 2 minutes at 15,000 rpm, and then an aliquot thereof was used for HPLC analysis as in Example 1 to detect and quantify the compound (VIII-a) (wherein $R^1$ is Na). The concentration of the compound (VIII-a) in the reaction solution calculated based on the quantification result, is shown in Table 4.

TABLE 4

| Plasmid | Compound (VIII-a) (mg/l) |
| --- | --- |
| pRI109 | 0.3 |
| pSYN2-72 | 30 |
| pRIyjiB | 61 |
| pSYN2-39 | 104 |

EXAMPLE 6

Introduction of the Plasmid into Coryne-Form Bacteria and Evaluation of Activity pRIyjiB DNA obtained in Example 4 was introduced into C. callunae ATCC15991, C. ammoniagenes ATCC6872 and B. flavum ATCC14067 in the same manner as in the transformation of ATCC13032 strain described in Example 5, and transformants were obtained from each strain.

The obtained transformants were respectively inoculated on 3 ml of broth media in test tubes containing 100 µg/ml kanamycin, and cultured with shaking for 24 hours at 30° C. The culture (0.5 ml) was transferred to a test tube containing 5 ml TB medium [in which 14 g of Bacto Trypton (produced by Difco) and 24 g of Bacto Yeast Extract (produced by Difco) were dissolved in 900 ml of water and sterilized in an autoclave, to which 100 ml PB [$KH2PO_4$ 23.1 g/l, $K_2HPO_4$ 125.1 g/l] separately sterilized in an autoclave was added] wherein the medium contains 100 µg/ml kanamycin and 10 g/l Glucose, and cultured with shaking for 5 hours at 30° C. The culture (1 ml) was transferred to an assist tube (produced by ASSIST), and compound (VII-a) (wherein R is Na) was added thereto to the final concentration of 300 mg/l, and the mixture was reacted with shaking for 16 hours at 30° C.

Upon completion of reaction, compound (VIII-a) (wherein $R^1$ is Na) in the culture was detected and quantified in the method as in Example 2. The concentration of compound (VIII-a) in the culture calculated based on the quantification results, is shown in Table 5.

TABLE 5

| Host Cell | Plasmid | Compound (VIII-a) (mg/l) |
| --- | --- | --- |
| C. callunae ATCC15991 (KY3510) | pRIyjiB | 22 |
| C. ammoniagenes ATCC6872 (KY3454) | pRIyjiB | 12 |
| B. flavum ATCC14067 (KY10122) | pRIyjiB | 23 |

INDUSTRIAL APPLICABILITY

The present invention enables efficient production of a DNA encoding a novel hydroxylase and a compound inhibiting hydroxymethylglutaryl CoA (HMG-CoA) reductase and has an action of reducing serum cholesterol.

| Free Text of Sequence Listing | |
|---|---|
| SEQ ID NO:3 | synthetic DNA |
| SEQ ID NO:4 | synthetic DNA |
| SEQ ID NO:5 | synthetic DNA |
| SEQ ID NO:6 | synthetic DNA |
| SEQ ID NO:7 | synthetic DNA |
| SEQ ID NO:8 | synthetic DNA |
| SEQ ID NO:9 | synthetic DNA |
| SEQ ID NO:10 | synthetic DNA |
| SEQ ID NO:11 | synthetic DNA |
| SEQ ID NO:12 | synthetic DNA |
| SEQ ID NO:13 | synthetic DNA |
| SEQ ID NO:14 | synthetic DNA |
| SEQ ID NO:15 | synthetic DNA |
| SEQ ID NO:16 | synthetic DNA |
| SEQ ID NO:17 | synthetic DNA |
| SEQ ID NO:18 | synthetic DNA |
| SEQ ID NO:19 | synthetic DNA |
| SEQ ID NO:20 | synthetic DNA |
| SEQ ID NO:21 | synthetic DNA |
| SEQ ID NO:22 | synthetic DNA |

-continued

| Free Text of Sequence Listing | |
|---|---|
| SEQ ID NO:23 | synthetic DNA |
| SEQ ID NO:24 | synthetic DNA |
| SEQ ID NO:25 | synthetic DNA |
| SEQ ID NO:26 | synthetic DNA |
| SEQ ID NO:27 | synthetic DNA |
| SEQ ID NO:28 | synthetic DNA |
| SEQ ID NO:29 | synthetic DNA |
| SEQ ID NO:30 | synthetic DNA |
| SEQ ID NO:31 | synthetic DNA |
| SEQ ID NO:32 | synthetic DNA |
| SEQ ID NO:33 | synthetic DNA |
| SEQ ID NO:34 | synthetic DNA |
| SEQ ID NO:35 | synthetic DNA |
| SEQ ID NO:36 | synthetic DNA |
| SEQ ID NO:37 | synthetic DNA |
| SEQ ID NO:38 | synthetic DNA |
| SEQ ID NO:39 | synthetic DNA |
| SEQ ID NO:40 | synthetic DNA |

What is claimed is:

1. An isolated DNA having the nucleotide sequence shown by SEQ ID NO: 2.

2. A recombinant DNA vector comprising the DNA according to claim 1.

3. An isolated transformed cell obtained by introducing the recombinant DNA vector according to claim 2 into a host cell.

4. The transformed cell according to claim 3 wherein the transformed cell belongs to a microorganism selected from the genera *Escherichia, Bacillus, Corynebacterium*, and *Streptomyces*.

5. The transformed cell according to claim 3 wherein the transformed cell belongs to microorganism selected from *Escherichia coli, Bacillus subtilis, Bacillus megaterium, Corynebacterium glutamicum, Corynebacterium ammoniagenes, Corynebacterium callunae* and *Streptomyces lividans*.

6. A process for producing compound (II-a) or compound (II-b), wherein The transformed cell according to claim 3, a culture of the transformed cell, or a treated product of the culture is used as an enzyme source, and the process comprises:

allowing compound (I-a) or compound (I-b) to exist in an aqueous medium in the presence of the enzyme source;

allowing compound (II-a) or compound (II-b) to be produced and accumulated in said aqueous medium; and collecting compound (II-a) or compound (II-b) from said aqueous medium wherein, the compound (I-a) is a compound represented by the formula (I-a):

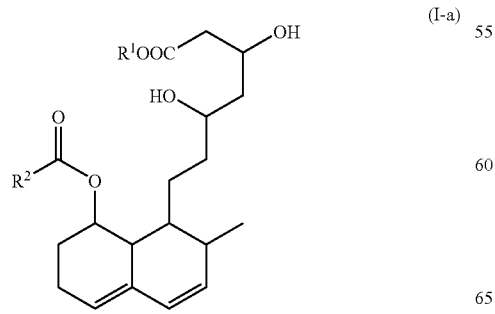
(I-a)

the compound (I-b) is a lactone form of compound (I-a) and is represented by the formula (I-b):

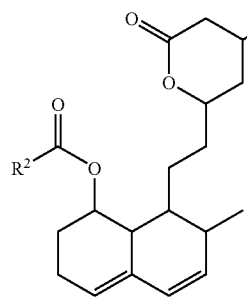
(I-b)

the compound (II-a) is a compound represented by the formula (II-a):

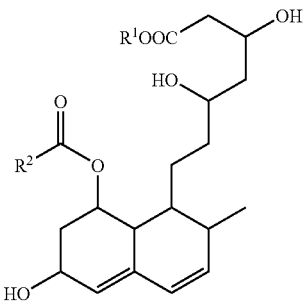
(II-a)

the compound (II-b) is a lactone form of compound (II-a) and is represented by the formula (II-b):

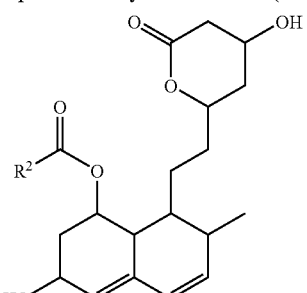
(II-b)

and wherein $R^1$ represents a hydrogen atom, a substituted or unsubstituted alkyl, or an alkali metal, and $R^2$ represents a substituted or unsubstituted alkyl, or a substituted or unsubstituted aryl; and wherein the treated product of the culture of the transformed cell is a treated product selected from cultured cells, dried cells, freeze-dried cells, cells treated with a surfactant, cells treated with an enzyme, cells treated by ultrasonication, cells treated by mechanical milling, cells treated by solvent, a protein fraction of a cell, and immobilized cells.

7. A process for producing compound (IV-a) or compound (IV-b), wherein the transformed cell according to claim 3, a culture of the transformed cell, or a treated product of the culture is used as an enzyme source, and the process comprises:

allowing compound (III-a) or compound (III-b) to exist in an aqueous medium in the presence of the enzyme source;

allowing compound (IV-a) or compound (IV-b) to be produced and accumulated in said aqueous medium; and collecting compound (IV-a) or compound (IV-b) from said aqueous medium wherein, the compound (III-a) is a compound represented by the formula (III-a):

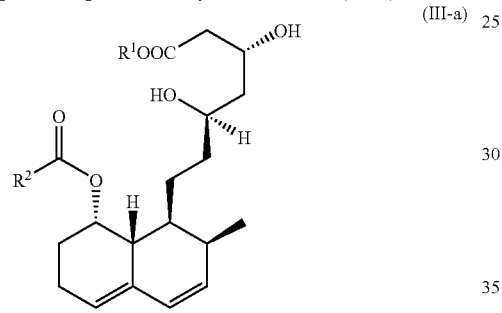

the compound (III-b) is a lactone form of compound (III-a) and is represented by the formula (III-b):

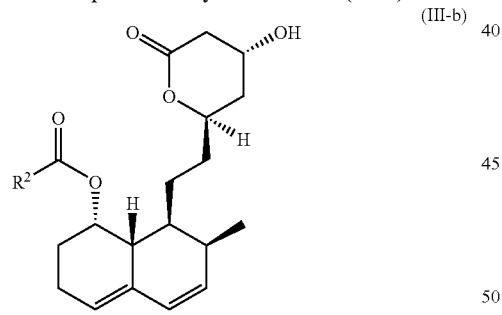

the compound (IV-a) is a compound represented by the formula (IV-a):

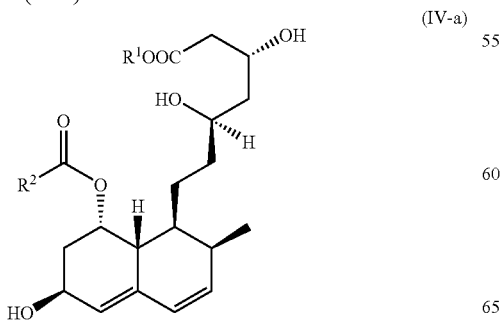

the compound (IV-b) is a lactone form of compound (IV-a) and is represented by the formula (IV-b):

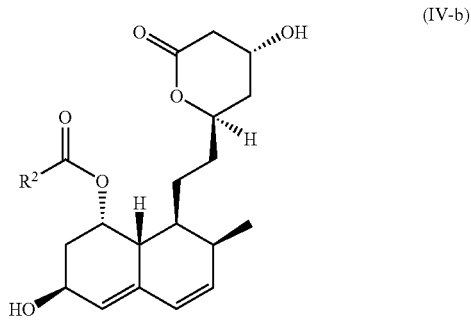

and wherein $R^1$ represents a hydrogen atom, a substituted or unsubstituted alkyl, or an alkali metal, and $R^2$ represents a substituted or unsubstituted alkyl, or a substituted or unsubstituted aryl; and wherein the treated product of the culture of the transformed cell is a treated product selected from cultured cells, dried cells, freeze-dried cells, cells treated with a surfactant, cells treated with an enzyme, cells treated by ultrasonication, cells treated by mechanical milling, cells treated by solvent, a protein fraction of a cell, and immobilized cells.

8. A process for producing compound (VI-a) or compound (VI-b), wherein the transformed cell according to claim 3, a culture of the transformed cell, or a treated product of the culture is used as an enzyme source, and the process comprises:

allowing compound (V-a) or compound (V-b) to exist in an aqueous medium in the presence of the enzyme source;

allowing compound (VI-a) or compound (VI-b) to be produced and accumulated in said aqueous medium; and collecting compound (VI-a) or compound (VI-b) from said aqueous medium wherein, the compound (V-a) is a compound represented by the formula (V-a):

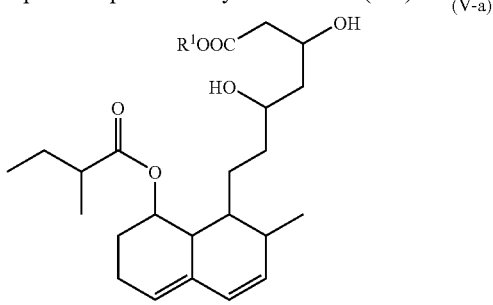

the compound (V-b) is a lactone form of compound (V-a) and is represented by the formula (V-b):

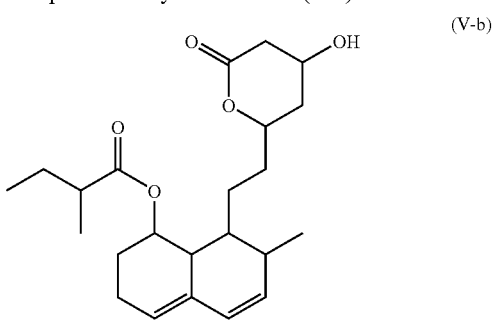

the compound (VI-a) is a compound represented by the formula (VI-a):

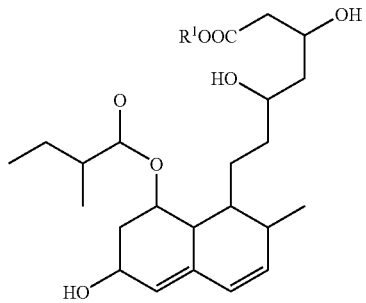
(VI-a)

the compound (VI-b) is a lactone form of compound (VI-a) and is represented by the formula (VI-b):

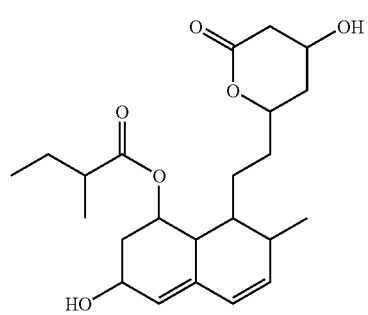
(VI-b)

and wherein $R^1$ represents a hydrogen atom, a substituted or unsubstituted alkyl, or an alkali metal; and wherein the treated product of the culture of the transformed cell is a treated product selected from cultured cells, dried cells, freeze-dried cells, cells treated with a surfactant, cells treated with an enzyme, cells treated by ultrasonication, cells treated by mechanical milling, cells treated by solvent, a protein fraction of a cell, and immobilized cells.

9. A process for producing compound (VIII-a) or compound (VIII-b), wherein the transformed cell according to claim 3, a culture of the transformed cell, or a treated product of the culture is used as an enzyme source, and the process comprises:

allowing compound (VII-a) or compound (VII-b) to exist in an aqueous medium in the presence of the enzyme source;

allowing compound (VII-a) or compound (VII-b) to be produced and accumulated in said aqueous medium; and collecting compound (VIII-a) or compound (VIII-b) from said aqueous medium wherein, the compound (VII-a) is a compound represented by the formula (VII-a):

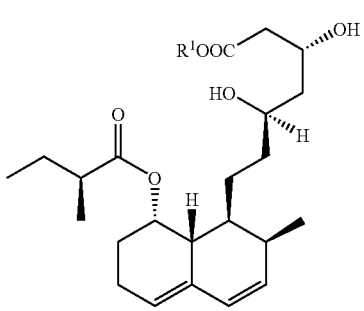
(VII-a)

the compound (VII-b) is a lactone form of compound (VII-a) and is represented by the formula (VII-b):

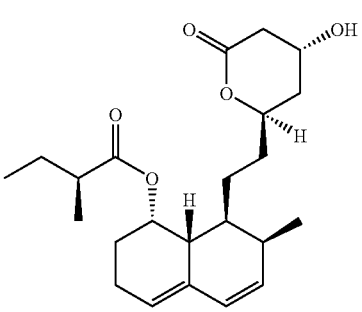
(VII-b)

the compound (VIII-a) is a compound represented by the formula (VIII-a):

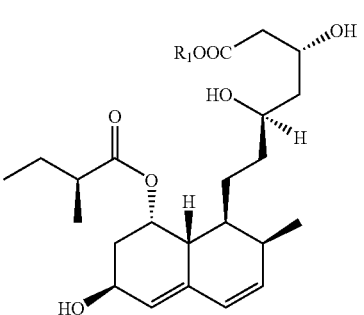
(VIII-a)

the compound (VII-b) is a lactone form of compound (VIII-a) and is represented by the formula (VIII-b):

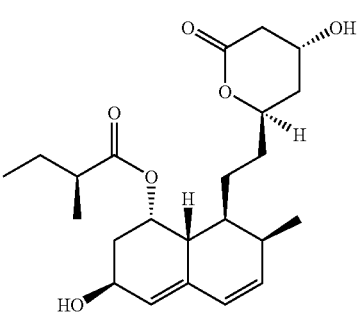
(VIII-b)

and wherein R¹ represents a hydrogen atom, a substituted or unsubstituted alkyl, or an alkali metal; and wherein the treated product of the culture of the transformed cell is a treated product selected from cultured cells, dried cells, freeze-dried cells, cells treated with a surfactant, cells treated with an enzyme, cells treated by ultrasonication, cells treated by mechanical milling, cells treated by solvent, a protein fraction of a cell, and immobilized cells.

10. The process according to claim 6, wherein the compound (II-b) is obtained by forming a lactone from compound (II-a), the compound (II-a) is a compound represented by the formula (II-a):

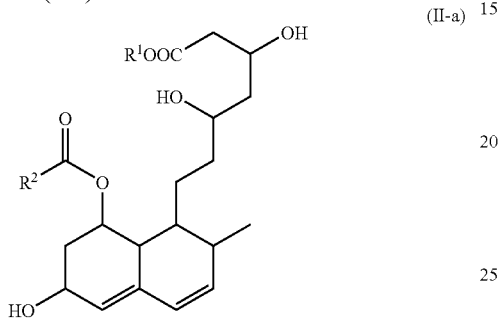

the compound (II-b) is a lactone form of compound (II-a) and is represented by the formula (II-b):

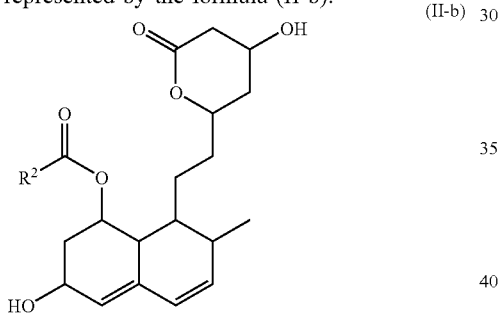

and wherein R¹ represents a hydrogen atom, a substituted or unsubstituted alkyl, or an alkali metal, and R² represents a substituted or unsubstituted alkyl, or a substituted or unsubstituted aryl.

11. The process according to claim 6, wherein the compound (II-a) is obtained by opening the lactone ring of compound (II-b), the compound (II-a) is a compound represented by the formula (II-a):

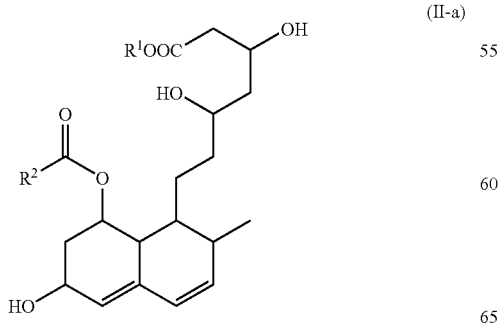

the compound (II-b) is a lactone form of compound (II-a) and is represented by the formula (II-b):

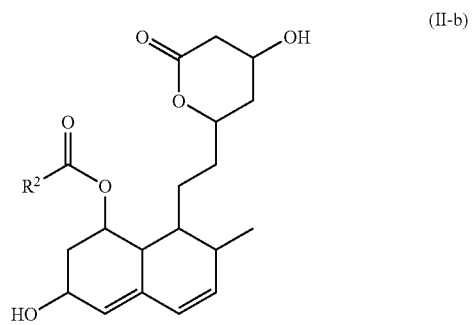

and wherein R¹ represents a hydrogen atom, a substituted or unsubstituted alkyl, or an alkali metal, and R² represents a substituted or unsubstituted alkyl, or a substituted or unsubstituted aryl.

12. The process according to claim 7, wherein the compound (IV-b) is obtained by forming a lactone from compound (IV-a), the compound (IV-a) is a compound represented by the formula (IV-a):

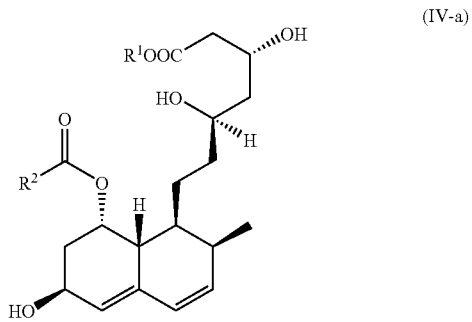

the compound (IV-b) is a lactone form of compound (IV-a) and is represented by the formula (IV-b):

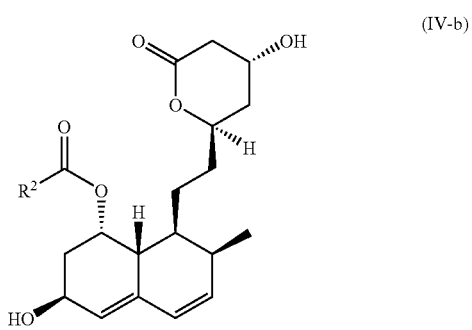

and wherein R¹ represents a hydrogen atom, a substituted or unsubstituted alkyl, or an alkali metal, and R² represents a substituted or unsubstituted alkyl, or a substituted or unsubstituted aryl.

13. The process according to claim 7, wherein the compound (IV-a) is obtained by opening the lactone ring of compound (IV-b), the compound (IV-a) is a compound represented by the formula (IV-a):

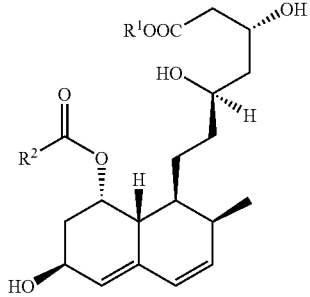
(IV-a)

the compound (IV-b) is a lactone form of compound (IV-a) and is represented by the formula (IV-b):

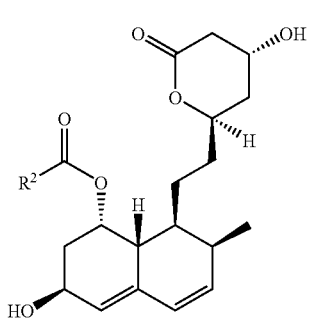
(IV-b)

and wherein $R^1$ represents a hydrogen atom, a substituted or unsubstituted alkyl, or an alkali metal, and $R^2$ represents a substituted or unsubstituted alkyl, or a substituted or unsubstituted aryl.

14. The process according to claim 8, wherein the compound (VI-b) is obtained by forming a lactone from compound (VI-a), the compound (IV-a) is a compound represented by the formula (IV-a):

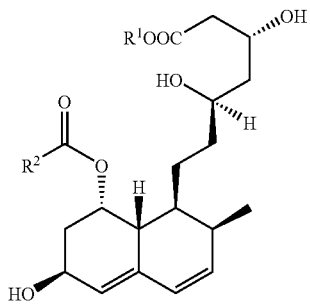
(IV-a)

the compound (IV-b) is a lactone form of compound (IV-a) and is represented by the formula (IV-b):

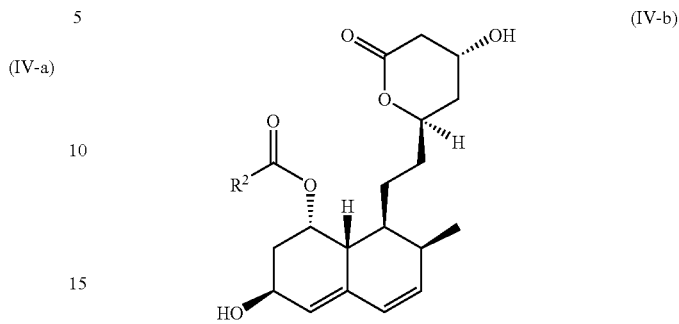
(IV-b)

and wherein $R^1$ represents a hydrogen atom, a substituted or unsubstituted alkyl, or an alkali metal, and $R^2$ represents a substituted or unsubstituted alkyl, or a substituted or unsubstituted aryl.

15. The process according to claim 8, wherein the compound (VI-a) is obtained by opening the lactone ring of compound (VI-b), the compound (VI-a) is a compound represented by the formula (VI-a):

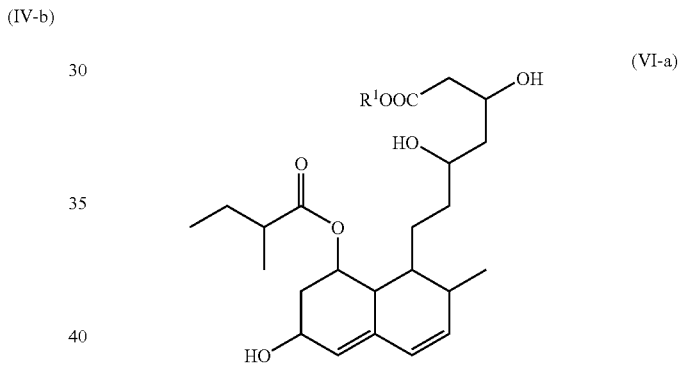
(VI-a)

the compound (VI-b) is a lactone form of compound (VI-a) and is represented by the formula (VI-b):

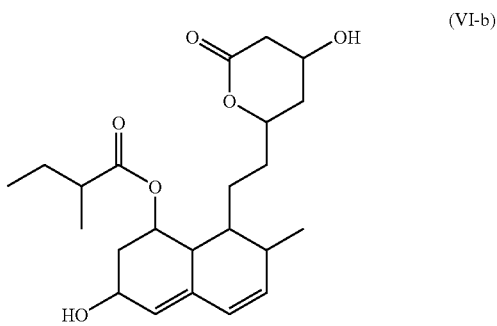
(VI-b)

and wherein $R^1$ represents a hydrogen atom, a substituted or unsubstituted alkyl, or an alkali metal.

16. The process according to claim 9, wherein the compound (VIII-b) is obtained by forming a lactone from compound (VIII-a), the compound (VIII-a) is a compound represented by the formula (VIII-a):

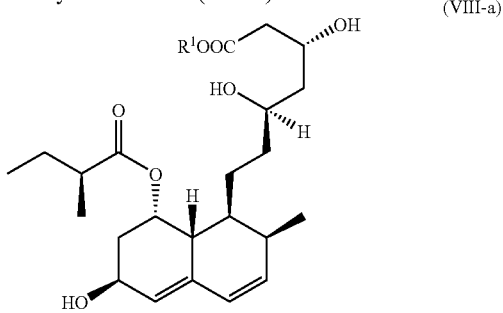
(VIII-a)

the compound (VIII-b) is a lactone form of compound (VIII-a) and is represented by the formula (VIII-b):

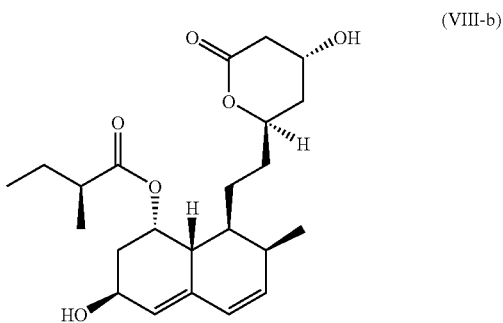
(VIII-b)

and wherein $R^1$ represents a hydrogen atom, a substituted or unsubstituted alkyl, or an alkali metal.

17. The process according to claim 9, wherein the compound (VIII-a) is obtained by opening the lactone ring of compound (VIII-b), the compound (VIII-a) is a compound represented by the formula (VIII-a):

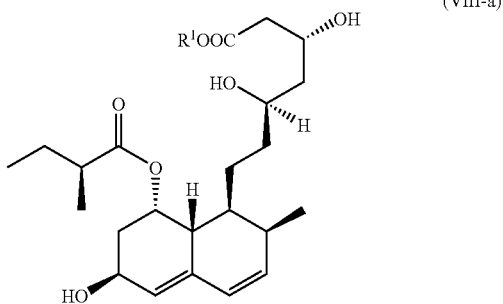
(VIII-a)

the compound (VIII-b) is a lactone form of compound (VIII-a) and is represented by the formula (VIII-b):

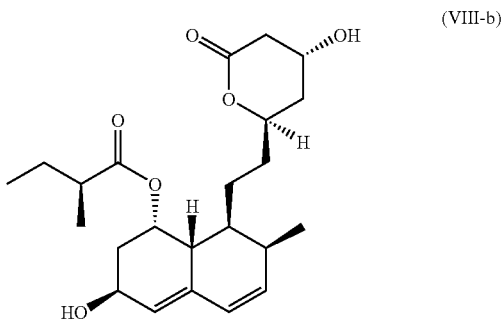
(VIII-b)

and wherein $R^1$ represents a hydrogen atom, a substituted or unsubstituted alkyl, or an alkali metal.

18. A process for producing a protein, which is derived from a microorganism belonging to the genus *Bacillus*, and has an activity of producing compound (II-a) or compound (II-b) from compound (I-a) or compound (I-b).

wherein the compound (I-a) is a compound represented by the formula (I-a):

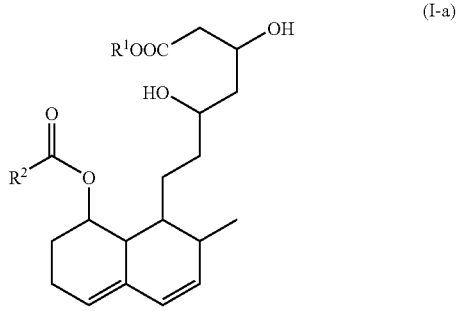
(I-a)

the compound (I-b) is a lactone form of compound (I-a) and is represented by the formula (I-b):

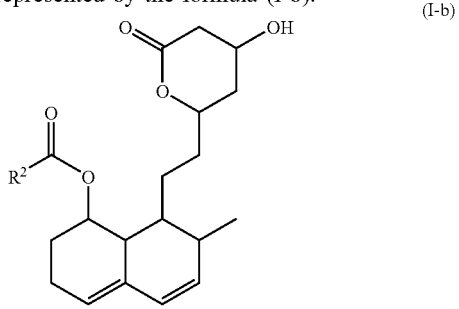
(I-b)

the compound (II-a) is a compound represented by the formula (II-a):

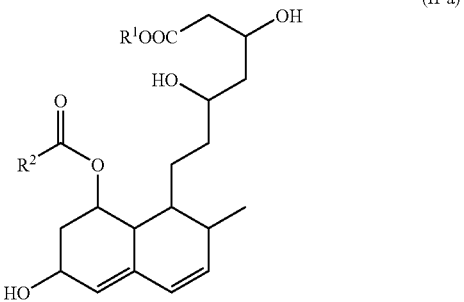
(II-a)

the compound (II-b) is a lactone form of compound (II-a) and is represented by the formula (II-b):

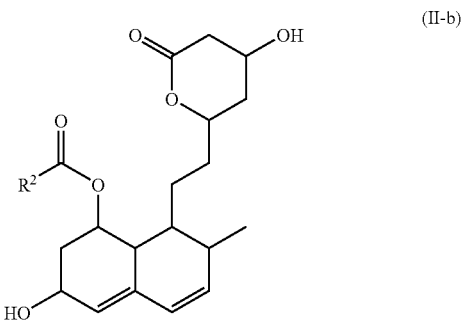
(II-b)

wherein $R^1$ represents a hydrogen atom, a substituted or unsubstituted alkyl, or an alkali metal, and $R^2$ represents a substituted or unsubstituted alkyl, or a substi tuted or unsubstituted aryl, which comprises culturing a transformed cell obtained by introducing a recombinant DNA vector comprising the DNA having the nucleotide sequence shown by SEQ ID NO: 2 in a medium; producing and accumulating the protein in the culture; and collecting the protein from said culture.

* * * * *

UNITED STATES PATENT AND TRADEMARK OFFICE
CERTIFICATE OF CORRECTION

PATENT NO. : 7,049,111 B1  
APPLICATION NO. : 09/869334  
DATED : May 23, 2006  
INVENTOR(S) : H. Endo et al.

Page 1 of 2

It is certified that error appears in the above-identified patent and that said Letters Patent is hereby corrected as shown below:

At column 55, line 41 (claim 6, line 2) of the printed patent, "The" should be --the--.

At column 59, lines 5-15 (claim 8, between lines 18 and 19) of the printed patent,

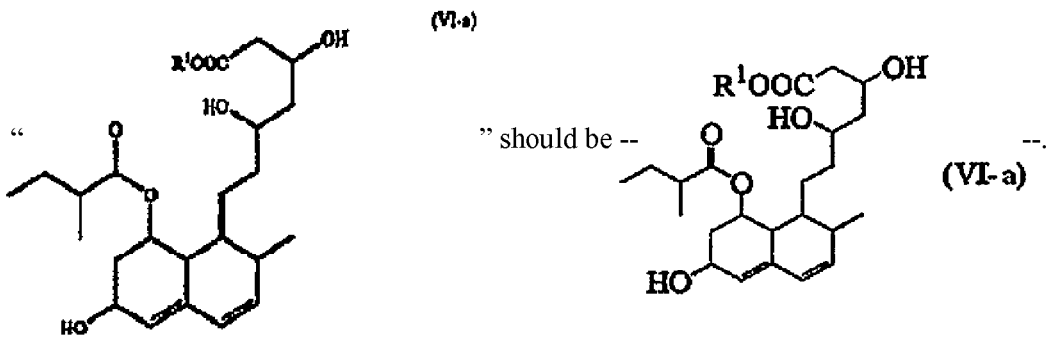

At column 59, line 61 (claim 9, line 9) of the printed patent, "(VII-a)" should be --(VIII-a)--.

At column 59, line 61 (claim 9, line 9) of the printed patent, "(VII-b)" should be --(VIII-b)--.

At column 60, lines 35-49 (claim 9, between lines 18 and 19) of the printed patent,

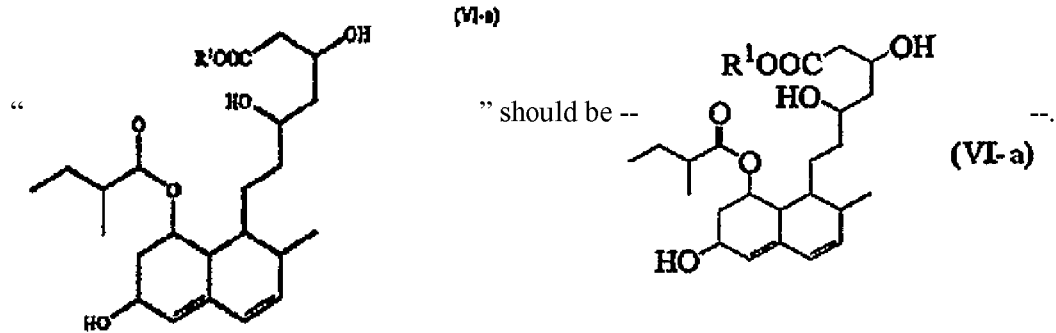

UNITED STATES PATENT AND TRADEMARK OFFICE
CERTIFICATE OF CORRECTION

PATENT NO. : 7,049,111 B1
APPLICATION NO. : 09/869334
DATED : May 23, 2006
INVENTOR(S) : H. Endo et al.

It is certified that error appears in the above-identified patent and that said Letters Patent is hereby corrected as shown below:

At column 60, line 51 (claim 9, line 19) of the printed patent, "(VII-b)" should be --(VIII-b)--.

Signed and Sealed this

Seventeenth Day of April, 2007

JON W. DUDAS
*Director of the United States Patent and Trademark Office*

SEQUENCE LISTING

```
<160> NUMBER OF SEQ ID NOS: 45

<210> SEQ ID NO 1
<211> LENGTH: 396
<212> TYPE: PRT
<213> ORGANISM: Bacillus subtilis

<400> SEQUENCE: 1

Met Asn Val Leu Asn Arg Arg Gln Ala Leu Gln Arg Ala Leu Leu Asn
1               5                  10                  15

Gly Lys Asn Lys Gln Asp Ala Tyr His Pro Phe Pro Trp Tyr Glu Ser
            20                  25                  30

Met Arg Lys Asp Ala Pro Val Ser Phe Asp Glu Glu Asn Gln Val Trp
        35                  40                  45

Ser Val Phe Leu Tyr Asp Asp Val Lys Lys Val Val Gly Asp Lys Glu
    50                  55                  60

Leu Phe Ser Ser Cys Met Pro Gln Gln Thr Ser Ser Ile Gly Asn Ser
65                  70                  75                  80

Ile Ile Asn Met Asp Pro Pro Lys His Thr Lys Ile Arg Ser Val Val
                85                  90                  95

Asn Lys Ala Phe Thr Pro Arg Val Met Lys Gln Trp Glu Pro Arg Ile
            100                 105                 110

Gln Glu Ile Thr Asp Glu Leu Ile Gln Lys Phe Gln Gly Arg Ser Glu
        115                 120                 125

Phe Asp Leu Val His Asp Phe Ser Tyr Pro Leu Pro Val Ile Val Ile
    130                 135                 140

Ser Glu Leu Leu Gly Val Pro Ser Ala His Met Glu Gln Phe Lys Ala
145                 150                 155                 160
```

```
Trp Ser Asp Leu Leu Val Ser Thr Pro Lys Asp Lys Ser Glu Glu Ala
            165                 170                 175
Glu Lys Ala Phe Leu Glu Glu Arg Asp Lys Cys Glu Glu Glu Leu Ala
            180                 185                 190
Ala Phe Phe Ala Gly Ile Ile Glu Gly Lys Arg Asn Lys Pro Glu Gln
            195                 200                 205
Asp Ile Ile Ser Ile Leu Val Glu Ala Glu Thr Gly Glu Lys Leu
            210                 215                 220
Ser Gly Glu Glu Leu Ile Pro Phe Cys Thr Leu Leu Val Ala Gly
225                 230                 235                 240
Asn Glu Thr Thr Thr Asn Leu Ile Ser Asn Ala Met Tyr Ser Ile Leu
            245                 250                 255
Glu Thr Pro Gly Val Tyr Glu Glu Leu Arg Ser His Pro Glu Leu Met
            260                 265                 270
Pro Gln Ala Val Glu Glu Ala Leu Arg Phe Arg Ala Pro Ala Pro Val
            275                 280                 285
Leu Arg Arg Ile Ala Lys Arg Asp Thr Glu Ile Gly Gly His Leu Ile
            290                 295                 300
Lys Glu Gly Asp Met Val Leu Ala Phe Val Ala Ser Ala Asn Arg Asp
305                 310                 315                 320
Glu Ala Lys Phe Asp Arg Pro His Met Phe Asp Ile Arg Arg His Pro
            325                 330                 335
Asn Pro His Ile Ala Phe Gly His Gly Ile His Phe Cys Leu Gly Ala
            340                 345                 350
Pro Leu Ala Arg Leu Glu Ala Asn Ile Ala Leu Thr Ser Leu Ile Ser
            355                 360                 365
Ala Phe Pro His Met Glu Cys Val Ser Ile Thr Pro Ile Glu Asn Ser
            370                 375                 380
Val Ile Tyr Gly Leu Lys Ser Phe Arg Val Lys Met
385                 390                 395

<210> SEQ ID NO 2
<211> LENGTH: 1191
<212> TYPE: DNA
<213> ORGANISM: Bacillus subtilis

<400> SEQUENCE: 2
atgaatgtgt taaaccgccg gcaagccttg cagcgagcgc tgctcaatgg gaaaaacaaa      60
caggatgcgt atcatccgtt tccatggtat gaatcgatga aaaggatgc gcctgtttcc     120 tttgatgaag aaaaccaagt gtggagcgtt tttctttatg atgatgtcaa aaaagttgtt     180
ggggataaag agttgttttc agttgcatg ccgcagcaga caagctctat tggaaattcc     240
atcattaaca tggacccgcc gaagcataca aaaatccgtt cagtcgtgaa caaagccttt     300
actccgcgcg tgatgaagca atgggaaccg agaattcaag aaatcacaga tgaactgatt     360
caaaaatttc aggggcgcag tgagtttgac cttgttcacg attttcata cccgcttccg     420 gttattgtga tatctgagct gctgggagtg ccttcagcgc agatggaaca gtttaaagca     480
tggtctgatc ttctggtcag tacaccgaag gataaaagtg aagaagctga aaagcctttt     540
ttggaagaac gagataagtg tgaggaagaa ctggccgcgt ttttgccgg catcatagaa     600 gaaaagcgaa acaaaccgga acaggatatt atttctattt tagtggaagc ggaagaaaca     660
ggcgagaagc tgtccggtga agagctgatt ccgttttgca cgctgctgct ggtggccgga     720
aatgaaacca ctacaaacct gatttcaaat gcgatgtaca gcatattaga aacgccaggc     780
```

```
gtttacgagg aactgcgcag ccatcctgaa ctgatgcctc aggcagtgga ggaagccttg      840
cgtttcagag cgccggcccc ggttttgagg cgcattgcca agcgggatac ggagatcggg      900
gggcacctga ttaaagaagg tgatatggtt ttggcgtttg tggcatcggc aaatcgtgat      960
gaagcaaagt tgacagacc gcacatgttt gatatccgcc gccatcccaa tccgcatatt      1020
gcgtttggcc acggcatcca ttttgcctt ggggccccgc ttgcccgtct tgaagcaaat      1080
atcgcgttaa cgtctttgat ttctgctttt cctcatatgg agtgcgtcag tatcactccg      1140
attgaaaaca gtgtgatata cggattaaag agcttccgtg tgaaaatgta a              1191
```

<210> SEQ ID NO 3
<211> LENGTH: 39
<212> TYPE: DNA
<213> ORGANISM: Artificial
<220> FEATURE:
<223> OTHER INFORMATION: PCR Primer

<400> SEQUENCE: 3

```
tttggatccg aattcaaaag tgctggcgct gttccgttt                            39
```

<210> SEQ ID NO 4
<211> LENGTH: 41
<212> TYPE: DNA
<213> ORGANISM: Artificial
<220> FEATURE:
<223> OTHER INFORMATION: PCR Primer

<400> SEQUENCE: 4

```
gtgggatccg tcgaccactt ttttcacgat gttcactccc c                         41
```

<210> SEQ ID NO 5
<211> LENGTH: 39
<212> TYPE: DNA
<213> ORGANISM: Artificial
<220> FEATURE:
<223> OTHER INFORMATION: PCR Primer

<400> SEQUENCE: 5

```
ccaggatcct ctagatggtg aaatggttgt tgccgctct                            39
```

<210> SEQ ID NO 6
<211> LENGTH: 39
<212> TYPE: DNA
<213> ORGANISM: Artificial
<220> FEATURE:
<223> OTHER INFORMATION: PCR Primer

<400> SEQUENCE: 6

```
tcaggatccc ccgggtgagc ggcaaatcca cccaccctg                            39
```

<210> SEQ ID NO 7
<211> LENGTH: 37
<212> TYPE: DNA
<213> ORGANISM: Artificial
<220> FEATURE:
<223> OTHER INFORMATION: PCR Primer

<400> SEQUENCE: 7

```
taagcgcgcc ccgggttaat tggatgggcg aaagctc                              37
```

<210> SEQ ID NO 8
<211> LENGTH: 39
<212> TYPE: DNA

<213> ORGANISM: Artificial
<220> FEATURE:
<223> OTHER INFORMATION: PCR Primer

<400> SEQUENCE: 8
atcgcgcgcg tcgacgatag cggcagaaaa ttggcggca              39

<210> SEQ ID NO 9
<211> LENGTH: 38
<212> TYPE: DNA
<213> ORGANISM: Artificial
<220> FEATURE:
<223> OTHER INFORMATION: PCR Primer

<400> SEQUENCE: 9
agcggatccg aattcgctgg aatcaaaagt cggccaga               38

<210> SEQ ID NO 10
<211> LENGTH: 38
<212> TYPE: DNA
<213> ORGANISM: Artificial
<220> FEATURE:
<223> OTHER INFORMATION: PCR Primer

<400> SEQUENCE: 10
tcaggatccg tcgactgaga aaacacaaac gcccctc                38

<210> SEQ ID NO 11
<211> LENGTH: 39
<212> TYPE: DNA
<213> ORGANISM: Artificial
<220> FEATURE:
<223> OTHER INFORMATION: PCR Primer

<400> SEQUENCE: 11
atgggatcct ctagacatgt tgtagtttgg gttggaatc              39

<210> SEQ ID NO 12
<211> LENGTH: 42
<212> TYPE: DNA
<213> ORGANISM: Artificial
<220> FEATURE:
<223> OTHER INFORMATION: PCR Primer

<400> SEQUENCE: 12
gccggatcca gatctggcat cacacaacaa taaatacacc gc          42

<210> SEQ ID NO 13
<211> LENGTH: 39
<212> TYPE: DNA
<213> ORGANISM: Artificial
<220> FEATURE:
<223> OTHER INFORMATION: PCR Primer

<400> SEQUENCE: 13
tctggatcct ctagaagaga acacaaagag tacgaatgc              39

<210> SEQ ID NO 14
<211> LENGTH: 41
<212> TYPE: DNA
<213> ORGANISM: Artificial
<220> FEATURE:
<223> OTHER INFORMATION: PCR Primer

<400> SEQUENCE: 14
aaaggatccc ccgggtttac cagccagcgc aacaaagtca t           41

<210> SEQ ID NO 15
<211> LENGTH: 39
<212> TYPE: DNA
<213> ORGANISM: Artificial
<220> FEATURE:
<223> OTHER INFORMATION: PCR Primer

<400> SEQUENCE: 15
cctgaattct ctagaaggct ttcaccacgt attttgctg                    39

<210> SEQ ID NO 16
<211> LENGTH: 41
<212> TYPE: DNA
<213> ORGANISM: Artificial
<220> FEATURE:
<223> OTHER INFORMATION: PCR Primer

<400> SEQUENCE: 16
tctgaattcc ccgggagaac aaaatgccaa aagcctgagt c                 41

<210> SEQ ID NO 17
<211> LENGTH: 34
<212> TYPE: DNA
<213> ORGANISM: Artificial
<220> FEATURE:
<223> OTHER INFORMATION: PCR Primer

<400> SEQUENCE: 17
aatactagta caattgcatc gtcaactgca tctt                         34

<210> SEQ ID NO 18
<211> LENGTH: 41
<212> TYPE: DNA
<213> ORGANISM: Artificial
<220> FEATURE:
<223> OTHER INFORMATION: PCR Primer

<400> SEQUENCE: 18
gtgggatccg tcgaccactt ttttcacgat gttcactccc c                 41

<210> SEQ ID NO 19
<211> LENGTH: 34
<212> TYPE: DNA
<213> ORGANISM: Artificial
<220> FEATURE:
<223> OTHER INFORMATION: PCR Primer

<400> SEQUENCE: 19
gaaactagtt cttcaaaaga aaaaagagt gtaa                          34

<210> SEQ ID NO 20
<211> LENGTH: 39
<212> TYPE: DNA
<213> ORGANISM: Artificial
<220> FEATURE:
<223> OTHER INFORMATION: PCR Primer

<400> SEQUENCE: 20
tcaggatccc ccgggtgagc ggcaaatcca cccaccctg                    39

<210> SEQ ID NO 21
<211> LENGTH: 34
<212> TYPE: DNA
<213> ORGANISM: Artificial
<220> FEATURE:

<223> OTHER INFORMATION: PCR Primer

<400> SEQUENCE: 21
taaactagta gccaatcgat taaattgttt agtg                                    34

<210> SEQ ID NO 22
<211> LENGTH: 34
<212> TYPE: DNA
<213> ORGANISM: Artificial
<220> FEATURE:
<223> OTHER INFORMATION: PCR Primer

<400> SEQUENCE: 22
ggaggtacct tatgccccgt caaacgcaac gaga                                    34

<210> SEQ ID NO 23
<211> LENGTH: 34
<212> TYPE: DNA
<213> ORGANISM: Artificial
<220> FEATURE:
<223> OTHER INFORMATION: PCR Primer

<400> SEQUENCE: 23
aggactagtc aaatggaaaa attgatgttt catc                                    34

<210> SEQ ID NO 24
<211> LENGTH: 38
<212> TYPE: DNA
<213> ORGANISM: Artificial
<220> FEATURE:
<223> OTHER INFORMATION: PCR Primer

<400> SEQUENCE: 24
tcaggatccg tcgactgaga aaacacaaac gccccctc                                38

<210> SEQ ID NO 25
<211> LENGTH: 34
<212> TYPE: DNA
<213> ORGANISM: Artificial
<220> FEATURE:
<223> OTHER INFORMATION: PCR Primer

<400> SEQUENCE: 25
ggtactagta aggaaacaag cccgattcct cagc                                    34

<210> SEQ ID NO 26
<211> LENGTH: 42
<212> TYPE: DNA
<213> ORGANISM: Artificial
<220> FEATURE:
<223> OTHER INFORMATION: PCR Primer

<400> SEQUENCE: 26
gccggatcca gatctggcat cacacaacaa taaatacacc gc                           42

<210> SEQ ID NO 27
<211> LENGTH: 38
<212> TYPE: DNA
<213> ORGANISM: Artificial
<220> FEATURE:
<223> OTHER INFORMATION: PCR Primer

<400> SEQUENCE: 27
ttggatccac tagtaatgtg ttaaaccgcc ggcaagcc                                38

```
<210> SEQ ID NO 28
<211> LENGTH: 41
<212> TYPE: DNA
<213> ORGANISM: Artificial
<220> FEATURE:
<223> OTHER INFORMATION: PCR Primer

<400> SEQUENCE: 28
aaaggatccc ccgggtttac cagccagcgc aacaaagtca t            41

<210> SEQ ID NO 29
<211> LENGTH: 34
<212> TYPE: DNA
<213> ORGANISM: Artificial
<220> FEATURE:
<223> OTHER INFORMATION: PCR Primer

<400> SEQUENCE: 29
atgactagta aacaggcaag cgcaatacct cagc                    34

<210> SEQ ID NO 30
<211> LENGTH: 34
<212> TYPE: DNA
<213> ORGANISM: Artificial
<220> FEATURE:
<223> OTHER INFORMATION: PCR Primer

<400> SEQUENCE: 30
tttggtacct tacattcctg tccaaacgtc tttc                    34

<210> SEQ ID NO 31
<211> LENGTH: 29
<212> TYPE: DNA
<213> ORGANISM: Artificial
<220> FEATURE:
<223> OTHER INFORMATION: PCR Primer

<400> SEQUENCE: 31
agcggtcgac aatgaatgtg ttaaaccgc                          29

<210> SEQ ID NO 32
<211> LENGTH: 29
<212> TYPE: DNA
<213> ORGANISM: Artificial
<220> FEATURE:
<223> OTHER INFORMATION: PCR Primer

<400> SEQUENCE: 32
acgcggatcc ttacattttc acacggaag                          29

<210> SEQ ID NO 33
<211> LENGTH: 24
<212> TYPE: DNA
<213> ORGANISM: Artificial
<220> FEATURE:
<223> OTHER INFORMATION: PCR Primer

<400> SEQUENCE: 33
cgccagggtt ttcccagtca cgac                               24

<210> SEQ ID NO 34
<211> LENGTH: 18
<212> TYPE: DNA
<213> ORGANISM: Artificial
<220> FEATURE:
<223> OTHER INFORMATION: PCR Primer
```

<400> SEQUENCE: 34
cgcaatatgc ggattggg                                                       18

<210> SEQ ID NO 35
<211> LENGTH: 18
<212> TYPE: DNA
<213> ORGANISM: Artificial
<220> FEATURE:
<223> OTHER INFORMATION: PCR Primer

<400> SEQUENCE: 35
tttccggcca ccagcagc                                                       18

<210> SEQ ID NO 36
<211> LENGTH: 18
<212> TYPE: DNA
<213> ORGANISM: Artificial
<220> FEATURE:
<223> OTHER INFORMATION: PCR Primer

<400> SEQUENCE: 36
taaccggaag cgggtatg                                                       18

<210> SEQ ID NO 37
<211> LENGTH: 18
<212> TYPE: DNA
<213> ORGANISM: Artificial
<220> FEATURE:
<223> OTHER INFORMATION: PCR Primer

<400> SEQUENCE: 37
aaggaaacag gcgcatcc                                                       18

<210> SEQ ID NO 38
<211> LENGTH: 67
<212> TYPE: DNA
<213> ORGANISM: Artificial
<220> FEATURE:
<223> OTHER INFORMATION: PCR Primer

<400> SEQUENCE: 38
tcgcctcgag tcgaggaggt cgactaatat gaacgttctg aaccgccgtc aagccttgca         60
gcgagcg                                                                   67

<210> SEQ ID NO 39
<211> LENGTH: 28
<212> TYPE: DNA
<213> ORGANISM: Artificial
<220> FEATURE:
<223> OTHER INFORMATION: PCR Primer

<400> SEQUENCE: 39
tcgcggatcc ttacattttc acacggaa                                            28

<210> SEQ ID NO 40
<211> LENGTH: 715
<212> TYPE: DNA
<213> ORGANISM: Artificial
<220> FEATURE:
<223> OTHER INFORMATION: Promoter Sequence

<400> SEQUENCE: 40
cctgcaggtc atcacccgag caggcgaccc gaacgttcgg aggctcctcg ctgtccattc         60
gctcccctgg cgcggtatga accgccgcct catagtgcag tttgatcctg acgagcccag        120

-continued

```
catgtctgcg cccaccttcg cggaacctga ccagggtccg ctagcgggcg gccggaaggt    180
gaatgctagg catgatctaa ccctcggtct ctggcgtcgc gactgcgaaa tttcgcgagg    240
gtttccgaga aggtgattgc gcttcgcaga tctcgtggac ggcttggttg acgccctccg    300
cccattgggt gatggtggca ccatttggct gttgactcct ggtgcaggaa aacgtggaac    360
tattgctcca ggtgaaattt ccgaatccgc acaattggca ggcctcgtcc agaccaccgc    420
agagcgtctc ggtgattggc agggcagctg cttggtcgcg cgcggcgcga tgaagaagta    480
agaattagcc gaaaacacct tccagccagg cgatttgctt aagttagaag gtgtggctag    540
tattctaaga gtgctcatga ggaagcgaaa gcttttaag agagcatgat gcggcttag    600 ctcagctgga agagcaactg gtttacaccc agtaggtcgg gggttcgatc cagctgtgaa    660
caattgcact ttggatctaa ttaagggatt agtcgactat ggatccccgg gtacc         715
```

<210> SEQ ID NO 41
<211> LENGTH: 1204
<212> TYPE: DNA
<213> ORGANISM: Bacillus subtilis

<400> SEQUENCE: 41

```
gtcgacaatg aatgtgttaa accgccggca agccttgcag cgagcgctgc tcaatgggaa     60
aaacaaacag gatgcgtatc atccgttttcc atggtatgaa tcgatgagaa aggatgcgcc   120
tgtttccttt gatgaagaaa accaagtgtg gagcgttttt ctttatgatg atgtcaaaaa   180
agttgttggg gataaagagt tgttttccag ttgcatgccg cagcagacaa gctctattgg   240
aaattccatc attaacatgg acccgccgaa gcatacaaaa atccgttcag tcgtgaacaa   300
agcctttact ccgcgcgcga tgaagcaatg ggaaccgaga attcaagaaa tcacagatga   360
actgattcaa aaatttcagg ggcgcagtga gtttgacctt gttcacgatt tttcataccc    420
gcttccggtt attgtgatat ctgagctgct gggagtgcct tcagcgcata tggaacagtt   480
taaagcatgg tctgatcttc tggtcagtac accgaaggat aaaagtgaag aagctgaaaa   540 agccttttttg gaagaacgag ataagtgtga ggaagaactg gccgcgttttt ttgccggcat   600 catagaagaa aagcgaaaca aaccggaaca ggatattat tctattttag tggaagcgga   660
agaaacaggc gagaagctgt ccggtgaaga gctgattccg ttgtgcacgc tgctgctggt   720
ggccggaaat gaaccactaa caaacctgat ttcaaatgcg atgtacagca tattagaaac   780
gccaggcgtt tacgaggaac tgcgcagcca tcctgaactg atgcctcagg cagtggagga   840
agccttgcgt ttcagagcgc cggccccggt tttgaggcgc attgccaagc gggatacgga   900
gatcgggggg cacctgatta agaaggtga tatggttttg gcgtttgtgg catcggcaaa   960
tcgtgatgaa gcaaagtttg acagaccgca catgttgat atccgccgcc atcccaatcc  1020
gcatattgcg tttggccacg gcatccattt ttgccttggg gccccgcttg cccgtcttga  1080
agcaaatatc gcgttaacgt ctttgatttc tgcttttcct catatggagt gcgtcagtat  1140
cactccgatt gaaaacagtg tgatatacgg attaaagagc ttccgtgtga aaatgtaagg  1200
atcc                                                              1204
```

<210> SEQ ID NO 42
<211> LENGTH: 396
<212> TYPE: PRT
<213> ORGANISM: Bacillus subtilis

<400> SEQUENCE: 42

```
Met Asn Val Leu Asn Arg Arg Gln Ala Leu Gln Arg Ala Leu Leu Asn
1               5                   10                  15
Gly Lys Asn Lys Gln Asp Ala Tyr His Pro Phe Pro Trp Tyr Glu Ser
            20                  25                  30
Met Arg Lys Asp Ala Pro Val Ser Phe Asp Glu Glu Asn Gln Val Trp
        35                  40                  45
Ser Val Phe Leu Tyr Asp Asp Val Lys Lys Val Val Gly Asp Lys Glu
50                  55                  60
Leu Phe Ser Ser Cys Met Pro Gln Gln Thr Ser Ile Gly Asn Ser
65                  70                  75                  80
Ile Ile Asn Met Asp Pro Pro Lys His Thr Lys Ile Arg Ser Val Val
                85                  90                  95
Asn Lys Ala Phe Thr Pro Arg Ala Met Lys Gln Trp Glu Pro Arg Ile
            100                 105                 110
Gln Glu Ile Thr Asp Glu Leu Ile Gln Lys Phe Gln Gly Arg Ser Glu
            115                 120                 125
Phe Asp Leu Val His Asp Phe Ser Tyr Pro Leu Pro Val Ile Val Ile
        130                 135                 140
Ser Glu Leu Leu Gly Val Pro Ser Ala His Met Glu Gln Phe Lys Ala
145                 150                 155                 160
Trp Ser Asp Leu Leu Val Ser Thr Pro Lys Asp Lys Ser Glu Glu Ala
                165                 170                 175
Glu Lys Ala Phe Leu Glu Arg Asp Lys Cys Glu Glu Glu Leu Ala
            180                 185                 190
Ala Phe Phe Ala Gly Ile Ile Glu Gly Lys Arg Asn Lys Pro Glu Gln
        195                 200                 205
Asp Ile Ile Ser Ile Leu Val Glu Ala Glu Thr Gly Glu Lys Leu
    210                 215                 220
Ser Gly Glu Glu Leu Ile Pro Leu Cys Thr Leu Leu Leu Val Ala Gly
225                 230                 235                 240
Asn Glu Thr Thr Thr Asn Leu Ile Ser Asn Ala Met Tyr Ser Ile Leu
                245                 250                 255
Glu Thr Pro Gly Val Tyr Glu Glu Leu Arg Ser His Pro Glu Leu Met
            260                 265                 270
Pro Gln Ala Val Glu Glu Ala Leu Arg Phe Arg Ala Pro Ala Pro Val
        275                 280                 285
Leu Arg Arg Ile Ala Lys Arg Asp Thr Glu Ile Gly Gly His Leu Ile
    290                 295                 300
Lys Glu Gly Asp Met Val Leu Ala Phe Val Ala Ser Ala Asn Arg Asp
305                 310                 315                 320
Glu Ala Lys Phe Asp Arg Pro His Met Phe Asp Ile Arg Arg His Pro
                325                 330                 335
Asn Pro His Ile Ala Phe Gly His Gly Ile His Phe Cys Leu Gly Ala
            340                 345                 350
Pro Leu Ala Arg Leu Glu Ala Asn Ile Ala Leu Thr Ser Leu Ile Ser
        355                 360                 365
Ala Phe Pro His Met Glu Cys Val Ser Ile Thr Pro Ile Glu Asn Ser
    370                 375                 380
Val Ile Tyr Gly Leu Lys Ser Phe Arg Val Lys Met
385                 390                 395
```

<210> SEQ ID NO 43
<211> LENGTH: 1221
<212> TYPE: DNA

<213> ORGANISM: Bacillus subtilis

<400> SEQUENCE: 43

| | | | | | |
|---|---|---|---|---|---|
| ctcgagtcga | ggaggtcgac | taatatgaac | gttctgaacc | gccgtcaagc | cttgcagcga | 60 |
| gcgctgctca | atgggaaaaa | caaacaggat | gcgtatcatc | cgtttccatg | gtatgaatcg | 120 |
| atgagaaagg | atgcgcctgt | tcctttgat | gaagaaaacc | aagtgtggag | cgttttcctt | 180 |
| tatgatgatg | tcaaaaaagt | tgttggggat | aaagagttgt | tttccagttg | catgccgcag | 240 |
| cagacaagct | ctattggaaa | ttccatcatt | aacatggacc | cgccgaagca | tacaaaaatc | 300 |
| cgttcagtcg | tgaacaaagc | ctttactccg | cgcgtgatga | agcaatggga | accgagaatt | 360 |
| caagaaatca | cagatgaact | gattcaaaaa | tttcaggggc | gcagtgagtt | tgaccttgtt | 420 |
| cacgattttt | catacccgct | tccggttatt | gtgatatctg | agctgctggg | agtgccttca | 480 |
| gcgcatatgg | aacagtttaa | agcatggtct | gatcttctgg | tcagtacacc | gaaggataaa | 540 |
| agtgaagaag | ctgaaaaagc | cttttttggaa | gaacgagata | agtgtgagga | agaactggcc | 600 |
| gcgttttttg | ccggcatcat | agaagaaaag | cgaaacaaac | cggaacagga | tattatttct | 660 |
| attttagtgg | aagcggaaga | aacaggcgag | aagctgtccg | gtgaagagct | gattccgttt | 720 |
| tgcacgctgc | tgctggtggc | cggaaatgaa | accactacaa | acctgatttc | aaatgcgatg | 780 |
| tacagcatat | agaaacgcc | aggcgtttac | gaggaactgc | gcagccatcc | tgaactgatg | 840 |
| cctcaggcag | tggaggaagc | cttgcgtttc | agagcgccgg | ccccggtttt | gaggcgcatt | 900 |
| gccaagcggg | atacggagat | cgggggcac | ctgattaaag | aaggtgatat | ggttttggcg | 960 |
| tttgtggcat | cggcaaatcg | tgatgaagca | aagtttgaca | accgcacat | gtttgatatc | 1020 |
| cgccgccatc | ccaatccgca | tattgcgttt | ggccacggca | tccatttttg | ccttggggcc | 1080 |
| ccgcttgccc | gtcttgaagc | aaatatcgcg | ttaacgtctt | tgatttctgc | ttttcctcat | 1140 |
| atggagtgcg | tcagtatcac | tccgattgaa | aacagtgtga | tatacggatt | aaagagcttc | 1200 |
| cgtgtgaaaa | tgtaaggatc | c | | | | 1221 |

<210> SEQ ID NO 44
<211> LENGTH: 1221
<212> TYPE: DNA
<213> ORGANISM: Bacillus subtilis

<400> SEQUENCE: 44

| | | | | | |
|---|---|---|---|---|---|
| ctcgagtcga | ggaggtcgac | taatatgaac | gttctgaacc | gccgtcaagc | cttgccgcga | 60 |
| gcgctgctca | atgggaaaaa | caaacaggat | gcgtatcatc | cgtttccatg | gtatgaatcg | 120 |
| atgagaaagg | atgcgcctgt | tcctttgat | gaagaaaacc | aagtgtggag | cgttttcctt | 180 |
| tatgatgatg | tcaaaaaagt | tgttggggat | aaagagttgt | tttccagttg | catgccgcag | 240 |
| cagacaagct | ctattggaaa | ttccatcatt | agcatggacc | cgccgaagca | tacaaaaatc | 300 |
| cgttcagtcg | tgaacaaagc | ctttactccg | cgcgcgatga | agcaatggga | accgagaatt | 360 |
| caagaaatca | cagatgaact | gattcaaaaa | tttcaggggc | gcagtgagtt | tgaccttgtt | 420 |
| cacgattatt | catacccgct | tccggttatt | gtgatatctg | agctgctggg | agtgccttca | 480 |
| gcgcatatgg | aacagtttaa | agcatggtct | gatcttctgg | tcagtacacc | gaaggataaa | 540 |
| agtgaagaag | ctgaaaaagc | cttttttggaa | gaacgagata | agtgtgagga | agaactggcc | 600 |
| gcgttttttg | ccggcatcat | agaagaaaag | cgaaacaaac | cggaacagga | tattatttct | 660 |
| attttagtgg | aagcggaaga | aacaggcgag | aagctgtccg | gtgaagagct | gattccgttg | 720 |
| tgcacgctgc | tgctggtggc | cggaaatgaa | accactacaa | acctgatttc | aaatgcgatg | 780 |

```
ttcagcatat tagaaacgcc aggcgtttac gaggaactgc gcagccatcc tgaactgatg      840
ccccaggcag tggaggaagc cttgcgtttc agagcgccgg ccccggtttt gaggcgcatt      900
gccaagcggg atacggagat cgggggggcac ctgattaaag aaggtgatac ggttttggcg     960
tttgtggcat cggcaaatcg tgatgaagca agtttgaca  gaccgcacat gtttgatatc     1020
cgccgccatc ccaatccgca tattgcgttt ggccacggca tccattttttg ccttggggcc    1080 ccgcttgccc gtcttgaagc aaatatcgcg ttaacgtctt tgatttctgc ttttcctcat     1140
atggagtgcg tcagtatcac tccgattgaa aacagtgtga tatacggatt aaagagcttc     1200
cgtgtgaaaa tgtaaggatc c                                               1221
```

<210> SEQ ID NO 45
<211> LENGTH: 396
<212> TYPE: PRT
<213> ORGANISM: Bacillus subtilis

<400> SEQUENCE: 45

```
Met Asn Val Leu Asn Arg Arg Gln Ala Leu Pro Arg Ala Leu Leu Asn
1               5                   10                  15

Gly Lys Asn Lys Gln Asp Ala Tyr His Pro Phe Pro Trp Tyr Glu Ser
            20                  25                  30

Met Arg Lys Asp Ala Pro Val Ser Phe Asp Glu Glu Asn Gln Val Trp
        35                  40                  45

Ser Val Phe Leu Tyr Asp Asp Val Lys Lys Val Gly Asp Lys Glu
    50                  55                  60

Leu Phe Ser Ser Cys Met Pro Gln Gln Thr Ser Ile Gly Asn Ser
65                  70                  75                  80

Ile Ile Ser Met Asp Pro Pro Lys His Thr Lys Ile Arg Ser Val Val
                85                  90                  95

Asn Lys Ala Phe Thr Pro Arg Ala Met Lys Gln Trp Glu Pro Arg Ile
            100                 105                 110

Gln Glu Ile Thr Asp Glu Leu Ile Gln Lys Phe Gln Gly Arg Ser Glu
        115                 120                 125

Phe Asp Leu Val His Asp Tyr Ser Tyr Pro Leu Pro Val Ile Val Ile
    130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Glu Leu Ala
            180                 185                 190

Ala Phe Phe Ala Gly Ile Ile Glu Glu Lys Arg Asn Lys Pro Glu Gln
        195                 200                 205

Asp Ile Ile Ser Ile Leu Val Glu Ala Glu Thr Gly Glu Lys Leu
    210                 215                 220

Ser Gly Glu Glu Leu Ile Pro Leu Cys Thr Leu Leu Val Ala Gly
225                 230                 235                 240

Asn Glu Thr Thr Thr Asn Leu Ile Ser Asn Ala Met Phe Ser Ile Leu
                245                 250                 255

Glu Thr Pro Gly Val Tyr Glu Glu Leu Arg Ser His Pro Glu Leu Met
            260                 265                 270

Pro Gln Ala Val Glu Glu Ala Leu Arg Phe Arg Ala Pro Ala Pro Val
        275                 280                 285
```

-continued

```
Leu Arg Arg Ile Ala Lys Arg Asp Thr Glu Ile Gly Gly His Leu Ile
    290             295                 300

Lys Glu Gly Asp Thr Val Leu Ala Phe Val Ala Ser Ala Asn Arg Asp
305             310                 315                 320

Glu Ala Lys Phe Asp Arg Pro His Met Phe Asp Ile Arg Arg His Pro
                325                 330                 335

Asn Pro His Ile Ala Phe Gly His Gly Ile His Phe Cys Leu Gly Ala
            340                 345                 350

Pro Leu Ala Arg Leu Glu Ala Asn Ile Ala Leu Thr Ser Leu Ile Ser
        355                 360                 365

Ala Phe Pro His Met Glu Cys Val Ser Ile Thr Pro Ile Glu Asn Ser
    370                 375                 380

Val Ile Tyr Gly Leu Lys Ser Phe Arg Val Lys Met
385                 390                 395
```